United States Patent [19]
Bartz et al.

[11] Patent Number: 5,814,110
[45] Date of Patent: Sep. 29, 1998

[54] CHEMICAL COMPOSITIONS AND USE AS FUEL ADDITIVES

[75] Inventors: Kenneth William Bartz, Baytown, Tex.; Jacqueline Dawn Bland, Wantage, United Kingdom; David Paul Gillingham, Swindon, United Kingdom; Richard Dix Kerwood, Didcot, United Kingdom; Edwin William Lehmann, Faringdon, United Kingdom; Kenneth Lewtas, Wantage, United Kingdom; John Edward Maddox, Swindon, United Kingdom; Albert Rossi, Warren, N.J.; Robert Dryden Tack, Abingdon, United Kingdom

[73] Assignee: Exxon Chemical Patents Inc., Linden, N.J.

[21] Appl. No.: 344,789

[22] Filed: Nov. 23, 1994

Related U.S. Application Data

[63] Continuation of Ser. No. 931,651, Aug. 17, 1992, abandoned, which is a continuation of Ser. No. 804,879, Dec. 6, 1991, abandoned, which is a continuation of Ser. No. 324,598, Mar. 16, 1989, abandoned, which is a continuation-in-part of Ser. No. 263,109, Oct. 26, 1988, abandoned, which is a continuation of Ser. No. 99,083, Sep. 21, 1987, abandoned, Ser. No. 248,364, Sep. 23, 1988, abandoned, and Ser. No. 248,664, Sep. 23, 1988, abandoned, which is a continuation of Ser. No. 99,085, Sep. 21, 1987, abandoned, said Ser. No. 248,364, is a continuation of Ser. No. 99,084, Sep. 21, 1987, abandoned.

[30] Foreign Application Priority Data

| Sep. 24, 1986 | [GB] | United Kingdom | 86-22959 |
| Sep. 24, 1986 | [GB] | United Kingdom | 86-22960 |
| Sep. 24, 1986 | [GB] | United Kingdom | 86-22961 |
| Aug. 17, 1987 | [GB] | United Kingdom | 87-19423 |

[51] Int. Cl.⁶ .............................. C10L 1/24; C10L 1/22; C10L 1/18

[52] U.S. Cl. .............................. 44/370; 44/371; 44/372; 44/374; 44/399; 44/405; 44/418; 44/419; 44/423; 558/46; 558/51; 560/12; 560/14; 560/129; 560/150; 562/45; 562/46; 562/58; 562/65; 562/84; 562/86; 562/90; 562/95; 562/105; 562/107; 562/111; 562/112; 562/114; 564/83; 564/84; 564/86; 564/90; 564/95

[58] Field of Search ............................. 44/370, 371, 372, 44/374, 399, 405, 418, 419, 423; 558/46, 51; 560/12, 14, 129, 150; 562/105, 107, 111, 112, 114, 45, 46, 58, 65, 84, 101; 564/83, 84, 86, 90, 95

[56] References Cited

U.S. PATENT DOCUMENTS

| 2,031,206 | 2/1936 | Bren | 564/84 |
| 2,197,851 | 4/1940 | Dietrich | 564/90 |
| 2,236,168 | 3/1941 | Dietrich | 564/90 |
| 2,289,760 | 7/1942 | Dickey et al. | 562/114 |
| 2,542,542 | 2/1951 | Lippincott et al. | |
| 2,683,736 | 7/1954 | Kosmin | 252/355 |
| 2,740,814 | 4/1956 | Cross et al. | 564/90 |
| 2,860,040 | 11/1958 | Fischl et al. | |
| 2,906,613 | 9/1959 | Mills | 44/423 |
| 3,048,479 | 8/1962 | Ilnyckyj et al. | |
| 3,055,928 | 9/1962 | Flores | 558/56 |
| 3,252,771 | 5/1966 | Clough et al. | |
| 3,481,939 | 12/1969 | Brannock | |
| 3,961,916 | 6/1976 | Ilnyckyj et al. | |
| 4,113,463 | 9/1978 | Oshio et al. | 564/85 |
| 4,211,534 | 7/1980 | Feldman | |
| 4,402,708 | 9/1983 | Oswald | 44/398 |
| 4,491,455 | 1/1985 | Ishizaki et al. | |
| 4,737,309 | 4/1988 | Kreevoy et al. | 564/90 |
| 5,017,610 | 5/1991 | Imaki et al. | 560/12 |
| 5,068,427 | 11/1991 | Sandler et al. | 564/84 |
| 5,102,427 | 4/1992 | Feldman et al. | 44/434 |
| 5,364,419 | 11/1994 | Tack et al. | 44/372 |

FOREIGN PATENT DOCUMENTS

| 0007590 A1 | 2/1980 | European Pat. Off. |
| 0049975 A2 | 4/1982 | European Pat. Off. |
| 0049976 A2 | 4/1982 | European Pat. Off. |
| 0061696 A2 | 10/1982 | European Pat. Off. |
| 0061894 A2 | 10/1982 | European Pat. Off. |
| 0061895 A2 | 10/1982 | European Pat. Off. |
| 0066953 A2 | 12/1982 | European Pat. Off. |
| 0071513 A2 | 2/1983 | European Pat. Off. |
| 0074208 A2 | 3/1983 | European Pat. Off. |
| 0100665 A2 | 2/1984 | European Pat. Off. |

(List continued on next page.)

OTHER PUBLICATIONS

Journal of Institute of Petroleum, "New Laboratory Text for Predicting Low-temperature Operability of Diesel Fuels" vol. 52, No. 510, Jun. 1966, pp. 173–185.

Industrial and Engineering Chemistry, "Crystal morphology in hydrocarbon systems" vol. 59, No. 5, May 1967, pp. 86–98.

Hydrocarbon Processing, "Blend for Lower Pour Point" vol. 54, No. 9, Sep. 1975, pp. 129–136.

Journal of the Institute of Petroleum, "Wax crystallization from distillate fuels. Part II. Mechanism of pour depression" Part III. Effect of wax composition on response to pour depressant and further development of the mechanism of pour depression vol. 51, No. 499, Jul. 1965, pp. 235–252.

"Molecular Mechanics", U. Berkert and N.L. Allinger ACS, 1982.

Proc. Roy. Soc. A., by A. Muller vol. 114, p. 542, 1927.
Proc. Roy. Soc. A., by A. Muller vol. 120, p. 437, 1928.
Proc. Roy. Soc. A., by A. Muller vol. 127, p. 417, 1930.
Proc. Roy. Soc. A., by A. Muller vol. 138, p. 514, 1932.
J. Chem. Phys., by A. E. Smith vol. 21, p. 2229, 1953.
Acta. Cryst., by P.W. Teare vol. 12, p. 294, 1959.

*Primary Examiner*—Jerry D. Johnson
*Attorney, Agent, or Firm*—John J. Mahon

[57] ABSTRACT

Distillate fuel is treated with additives whose structure match the crystal planes of the wax which crystallizes from the fuel to produce crystals below 4000 nanometres in size, suitable additive include novel sulpho-carboxylic materials particularly their esters and amine derivatives such as the amine salts and/or amides of ortho-sulpho benzoic acid.

13 Claims, 10 Drawing Sheets

FOREIGN PATENT DOCUMENTS

| | | |
|---|---|---|
| 0112195 A1 | 6/1984 | European Pat. Off. . |
| 0113581 A1 | 7/1984 | European Pat. Off. . |
| 0113582 A2 | 7/1984 | European Pat. Off. . |
| 0120512 A2 | 10/1984 | European Pat. Off. . |
| 0153176 A2 | 8/1985 | European Pat. Off. . |
| 0153177 A2 | 8/1985 | European Pat. Off. . |
| 0155807 A2 | 9/1985 | European Pat. Off. . |
| 0161082 A2 | 11/1985 | European Pat. Off. . |
| 2095712 | 11/1972 | France . |
| 2256235 | 12/1974 | France . |
| 2490669 | 9/1980 | France . |
| 3634083 | 4/1988 | Germany ............... 560/150 |
| 55-40640 | 10/1980 | Japan . |
| 56-54037 | 12/1981 | Japan . |
| 56-54038 | 12/1981 | Japan . |
| 1093686 | 12/1967 | United Kingdom ............ 562/114 |
| 1138553 | 1/1969 | United Kingdom . |
| 1263152 | 2/1972 | United Kingdom . |
| 1465175 | 2/1977 | United Kingdom . |
| 1465176 | 2/1977 | United Kingdom . |
| 1468588 | 3/1977 | United Kingdom . |
| 1469016 | 3/1977 | United Kingdom . |
| 1482685 | 8/1977 | United Kingdom . |
| 1486077 | 9/1977 | United Kingdom . |
| 1486144 | 9/1977 | United Kingdom . |
| 1549456 | 8/1979 | United Kingdom . |
| 1549457 | 8/1979 | United Kingdom . |
| 2028351 | 12/1980 | United Kingdom . |
| 2095698 | 10/1982 | United Kingdom . |
| 2096168 | 10/1982 | United Kingdom . |
| 2026507 | 12/1982 | United Kingdom . |
| 2129012 | 10/1983 | United Kingdom . |
| 2121807 | 1/1984 | United Kingdom . |
| 2121808 | 1/1984 | United Kingdom . |

Interchain distance d = 4.0 Å
Dihedral angle θ = 60°

Interchain distance d = 4.3 Å
Dihedral angle θ = 71°

Interchain distance d = 4.0 Å
Dihedral angle θ = 62.6°

Interchain distance d = 4.2 Å
Dihedral angle = 69°

θ ~ 80°

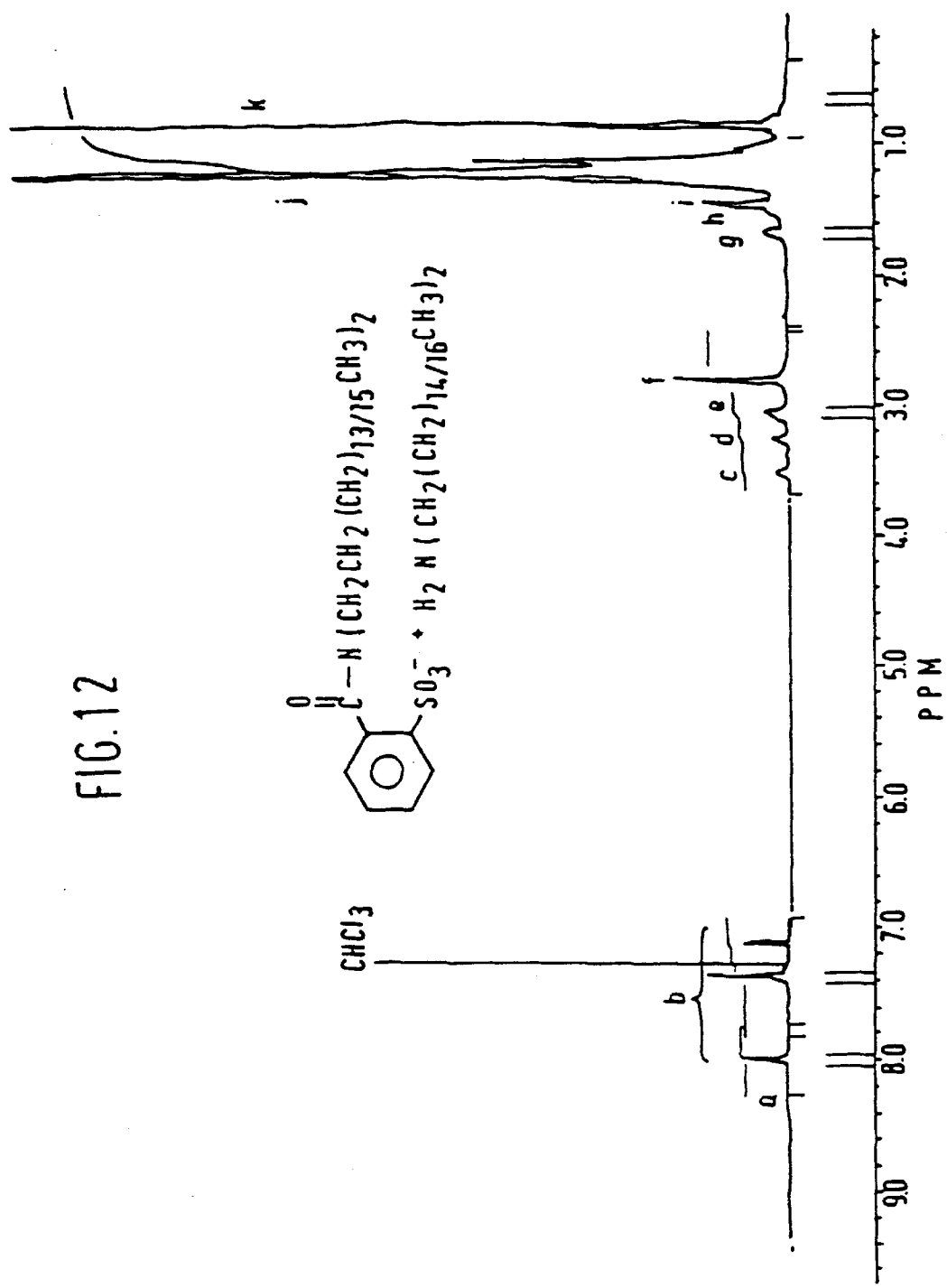

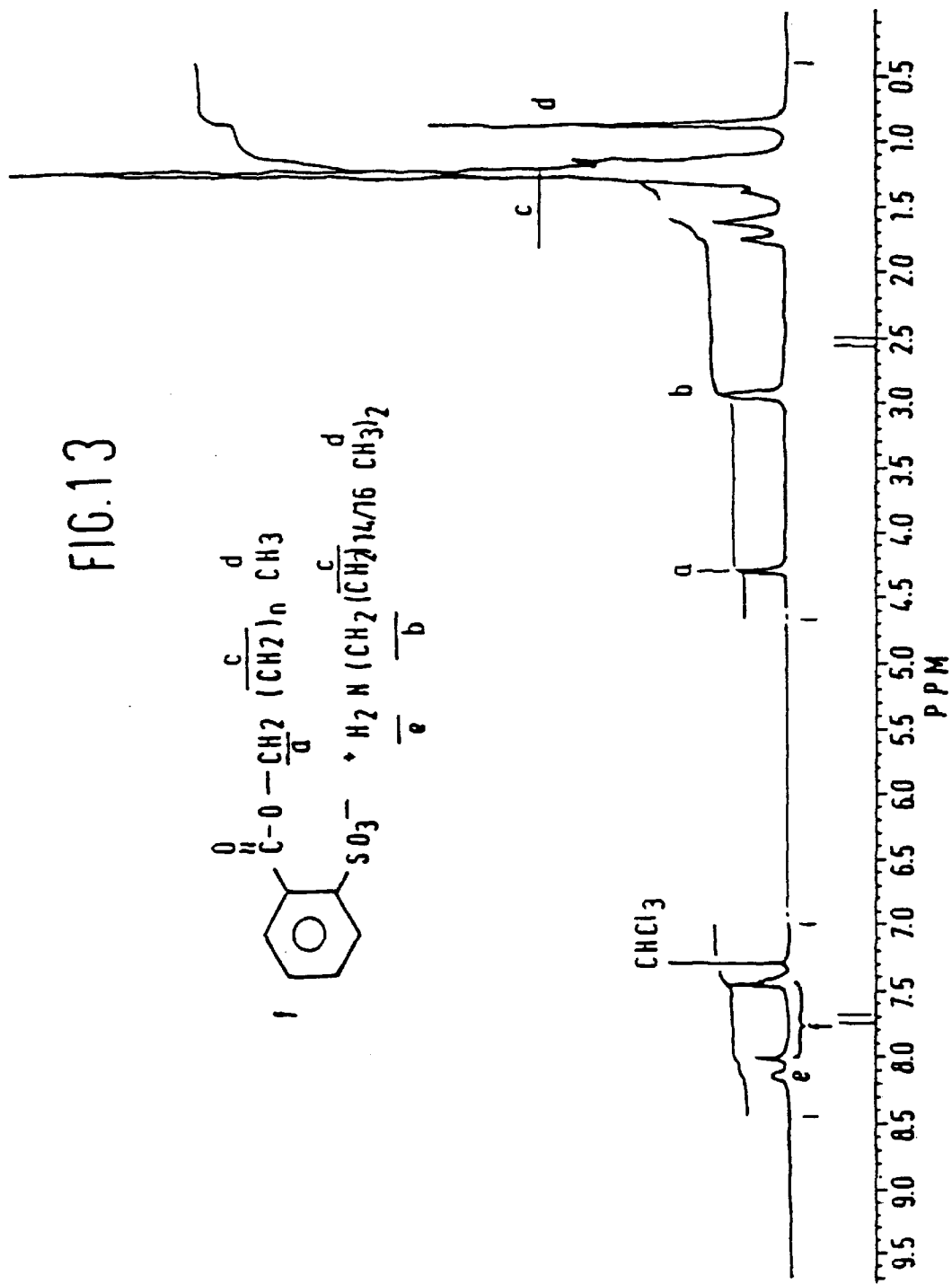

CHEMICAL COMPOSITIONS AND USE AS FUEL ADDITIVES

This is a continuation of application Ser. No. 07/931,651, filed Aug. 17, 1992, now abandoned, which is a Continuation of U.S. Ser. No. 804,879 filed Dec. 6, 1991, now abandoned, which is a Continuation of U.S. Ser. No. 324,598 filed Mar. 16, 1989, now abandoned, which is a Continuation In Part of U.S. Ser. No. 263,109 filed Oct. 26, 1988, now abandoned, which is a Continuation of U.S. Ser. No. 099,083 filed Sep. 21, 1987, now abandoned; and a continuation of U.S. Ser. No. 248,364 filed Sep. 23, 1988, abandoned which is a Continuation of U.S. Ser. No. 099,084 filed Sep. 23, 1987, now abandoned; and a continuation of U.S. Ser. No. 248,664 filed Aug. 23, 1988, now abandoned, which is a Continuation of U.S. Ser. No. 099,085, filed Sep. 21, 1987, now abandoned.

The invention relates to wax containing distillate fuel treated with additives whose structural configuration is particularly suited to the crystallography of the wax crystals which form in the distillate fuel as it cools, so that the additives interact with these waxes during crystallisation to produce precipitated wax of reduced crystal size. Whilst techniques such as chemical dewaxing, precipitation and filtration reduce the problems caused by wax these techniques are not required with the fuels of the present invention which have such small crystals.

In another aspect the invention relates to new chemical compounds which are useful as wax crystal modifiers in fuels especially distillate fuels, the use of these chemicals as distillate fuel additives and to fuels containing the additives.

Mineral oils containing paraffin wax have the characteristic of becoming less fluid as the temperature of the oil decreases. This loss of fluidity is due to the crystallisation of the wax into plate-like crystals which eventually form a spongy mass entrapping the oil therein. The temperature at which the wax crystals begin to form is known as the Cloud Point and the temperature at which the wax prevents the oil from pouring as the Pour Point. Between these temperatures the wax crystals can however block filters rendering systems such as diesel trucks and domestic heating systems inoperable.

It has long been known that various additives act as wax crystal modifiers when blended with waxy mineral oils. These compositions modify the size and shape of wax crystals and reduce the cohesive forces between the crystals and between the wax and the oil in such a manner as to permit the oil to remain fluid at lower temperature and in some instances to have improved filterability at temperatures between the cloud point and the pour point.

Various Pour Point depressants have been described in the literature and several of these are in commercial use. For example, U.S. Pat. No. 3,048,479 teaches the use of copolymers of ethylene and $C_1$–$C_5$ vinyl esters, e.g. vinyl acetate, as pour depressants for fuels, specifically heating oils, diesel and jet fuels. Hydrocarbon polymeric pour depressants based on ethylene and higher alpha-olefins, e.g. propylene, are also known.

U.S. Pat. No. 3,961,916 teaches the use of a mixture of copolymers, to control the size of the wax crystals and United Kingdom Patent 1,263,152 suggests that the size of the wax crystals may be controlled by using a copolymer having a low degree of side chain branching. Both systems improve the ability of the fuel to pass through filters as determined by the Cold Filter Plugging Point (CFPP) test since instead of plate like crystals formed without the presence of additives the needle shaped wax crystals produced will not block the pores of the filter rather forming a porous cake on the filter allowing passage of the remaining fluid.

Other additives have also been proposed for example, United Kingdom Patent 1,469,016, suggests that the copolymers of di-n-alkyl fumarates and vinyl acetate which have previously been used as pour depressants for lubricating oils may be used as co-additives with ethylene/vinyl acetate copolymers in the treatment of distillate fuels with high final boiling points to improve their low temperature flow properties.

U.S. Pat. No. 3,252,771 relates to the use of polymers of $C_{16}$ to $C_{18}$ alpha-olefins obtained by polymerising olefin mixtures that predominate in normal $C_{16}$ to $C_{18}$ alpha-olefins with aluminium trichloride/alkyl halide catalysts as pour depressants in distillate fuels of the broad boiling, easy-to-treat types available in the United States in the early 1960's.

It has also been proposed to use additives based on olefin/maleic anhydride copolymers. For example, U.S. Pat. No. 2,542,542 uses copolymers of olefins such as octadecene with maleic anhydride esterified with an alcohol such as lauryl alcohol as pour depressants and United Kingdom Patent 1,468,588 uses copolymers of $C_{22}$–$C_{28}$ olefins with maleic anhydride esterified with behenyl alcohol as co-additives for distillate fuels.

Similarly, Japanese Patent Publication 5,654,037 uses olefin/maleic anhydride copolymers which have been reacted with amines as pour point depressants and in Japanese Patent Publication 5,654,038 the derivatives of the olefin/maleic anhydride copolymers are used together with conventional middle distillate flow improvers such as ethylene vinyl acetate copolymers.

Japanese Patent Publication 5,540,640 discloses the use of olefin/maleic anhydride copolymers (not esterified) and states that the olefins used should contain more than 20 carbon atoms to obtain CFPP activity.

United Kingdom Patent 2,129,012 uses mixtures of esterified olefin/maleic anhydride copolymers and low molecular weight polyethylene, the esterified copolymers being ineffective when used as sole additives. The patent specifies that the olefin should contain 10–30 carbon atoms and the alcohol 6–28 carbon atoms with the longest chain in the alcohol containing 22–40 carbon atoms.

U.S. Pat. Nos. 3,444,082; 4,211,534; 4,375,973 and 4,402,708 suggest the use of certain nitrogen containing compounds.

Long n-alkyl derivatives of difunctional compounds have also been described as has their use as wax crystal modifiers for distillate fuels, to wit derivatives, particularly amine deriviatives of alkenyl succinic acid (U.S. Pat. No. 3,444,082), maleic acid (U.S. Pat. No. 4,211,534) and phthalic acid (GB 2,923,645, U.S. Pat. No. 4,375,973 and U.S. Pat. No. 4,402,708). Amine salts of certain alkylated aromatic sulphonic acids are described in United Kingdom Patent Specification 1,209,676 as is their use as antirust additives for turbine oils and hydraulic oils.

The improvement in CFPP activity achieved by the incorporation of the additives of these Patents is achieved by modifying the size and shape of the wax crystals forming to produce needle like crystals generally of particle size 10,000 nanometres or bigger typically 30,000 to 100,000 nanometres. In operation of diesel engines or heating systems at low temperatures, these crystals do not generally pass through the filters but form a permeable cake on the filter allowing the liquid fuel to pass, the wax crystals will subsequently dissolve as the engine and the fuel heats up, which can be by the bulk fuel being heated by recycled fuel. This can, however, result in the wax crystals blocking the filters, leading to starting problems and problems at the start of driving in cold weather or failure of fuel heating systems.

We have now found that the use as additives of compounds having a certain configuration and in particular certain novel compounds makes possible a significant reduction in the size of the wax crystals formed to below 4,000 nanometres sometimes below 2,000 nanometres and in some instances below 1,000 nanometres.

BRIEF DESCRIPTION OF THE DRAWINGS

FIG. 12 is a graph depicting the NMR spectroscopy analysis of the N,N-dialkyl ammonium salt of 2-dialkylamide benzene sulphonate prepared in accordance with Example 1;

FIG. 13 is a graph depicting the NMR spectroscopy analysis of the product of Example 2.

The wax precipitating from distillate fuels is mostly all normal alkanes which crystallize in an orthorhombic unit cell via a rotator or hexagonal form as is reported in the literature by for example, A. Muller in Proc. Roy. Soc. A. 114, 542, (1927), ibid. 120, 437, (1928 ibid.), 127, 417, (1930), ibid. 138, 514, (1932), A. E. Smith in J. Chem. Phys., 21, 2229, (1953) and P. W. Teare in Acta. Cryst., 12, 294, (1959). We have now found that the structure of effective additives for reducing crystal size can be determined with the aid of a computer, whereby it is possible to calculate accurately the geometry of the n-alkane wax crystal lattice and the energetically preferred geometry of a potential additive molecule in a simple and most convenient way. The results become especially clear when they are subsequently graphically represented with the aid of a plotter or a graphics terminal. This method is known as 'molecular modelling'.

Computer programs useful for this purpose are commercially available and a particularly useful series of programs is distributed by the firm Chemical Design Ltd., Oxford, England (Technical Director: E K Davies), under the designation 'Chem-X'.

Figure 1:
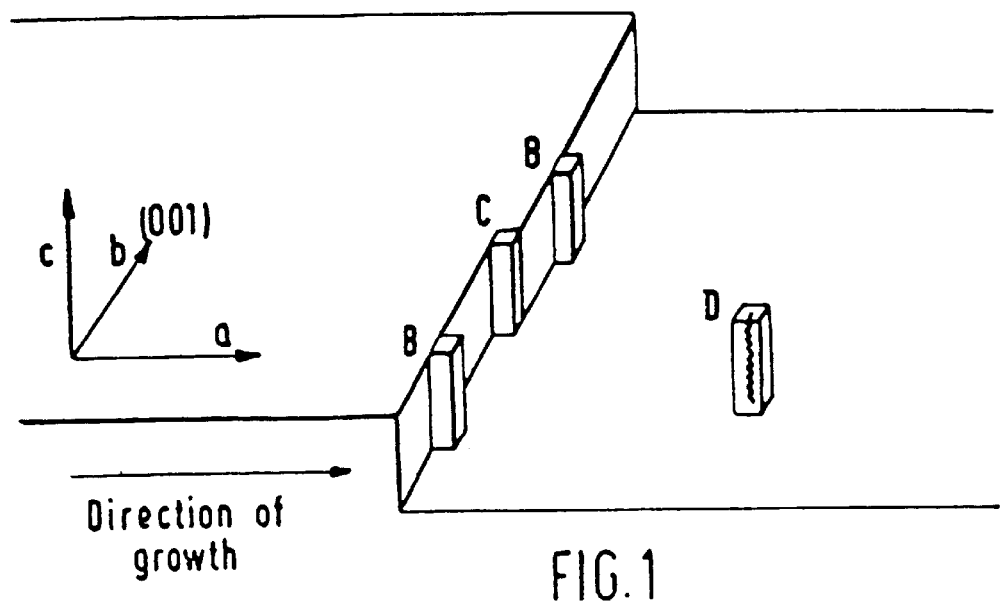
FIG. 1 is a schematic depiction of the growth of paraffin crystals taking place by association of single paraffin molecules with their long side to the edge of an existing paraffin platelet.
Figure 2:
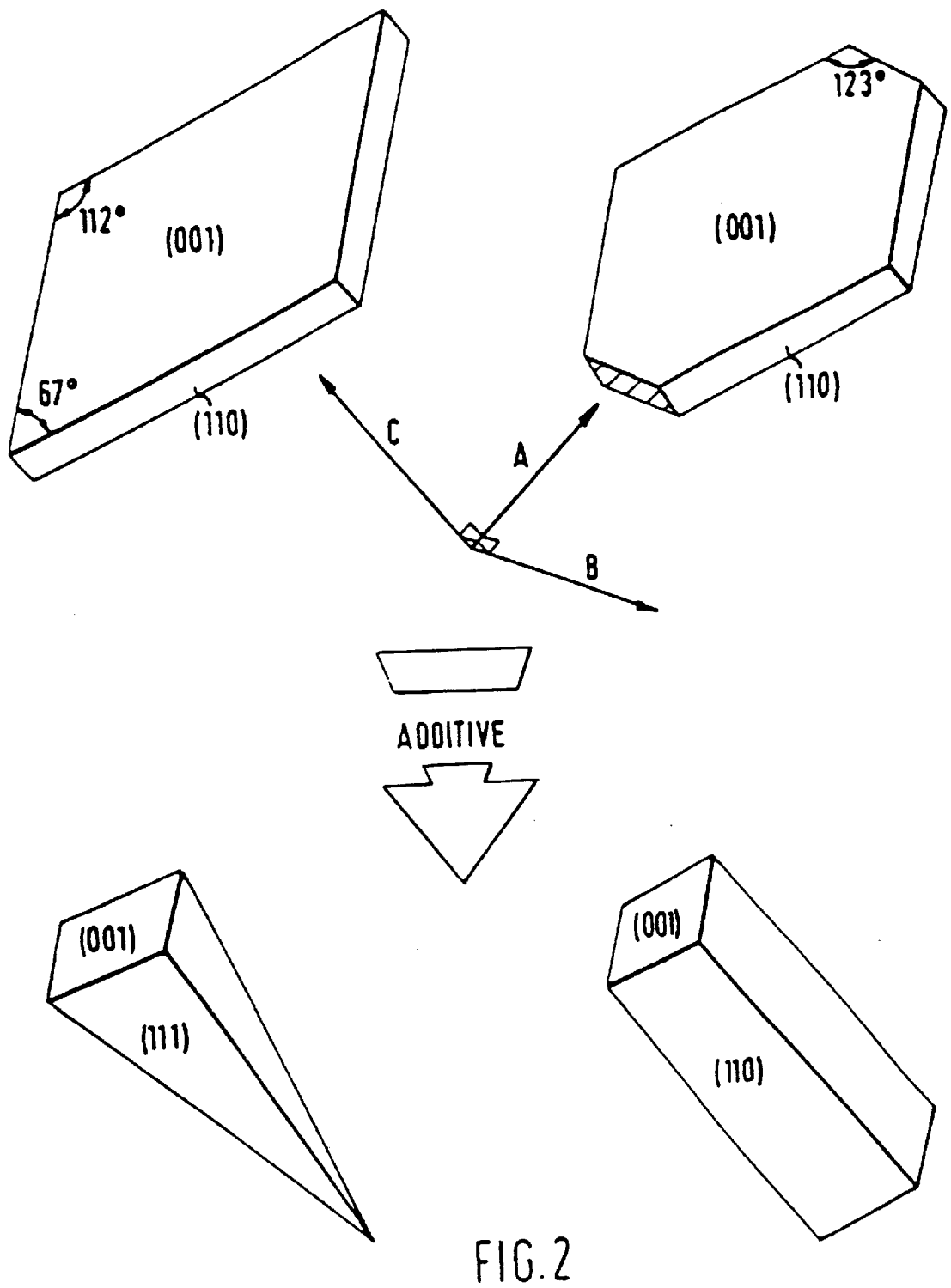
FIG. 2 schematically depicts that the association mainly occurs in the crystallographic plane.
Figure 3:
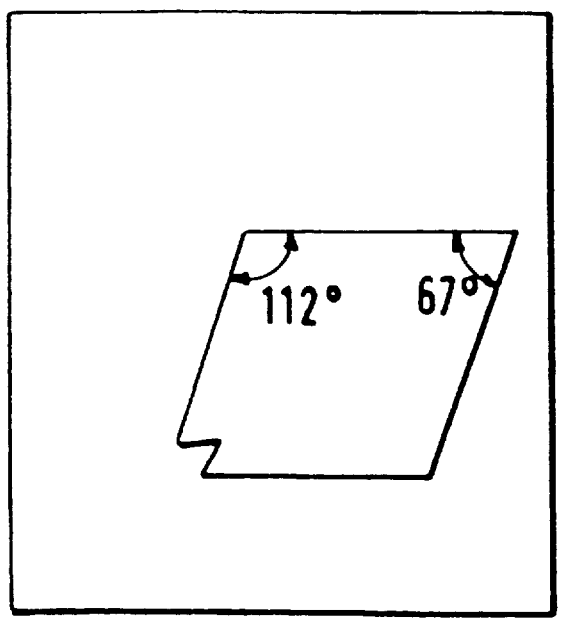
FIG. 3 schematically depicts the large flat rhombohedral plates formed by the crystals grown according to the present invention.

The growth of paraffin crystals takes place by association of single paraffin molecules with their long side to the edge of an existing paraffin platelet as is schematically shown in FIG. 1. The association to the top or bottom side of the platelet is energetically unfavourable because in this case, only one end of the paraffin chain molecule interacts with the existing crystal. The association mainly occurs in the crystallographic (001) plane (compare FIG. 2). Since the (001) plane contains the greatest number of strongest intermolecular bonds and thus the crystal grows to form large flat rhombohedral plates (FIG. 3). The next most stable face on the crystal is the (11x) (eg the (110)). The intermolecular association is strongest where the n-alkane molecules are closest, thus the (110) slice is stronger than the (100) slice.

The crystal grows by extending the (001) plane. Thus it is important to note that the edges of this plane are the rapidly advancing faces and these are the (11x) (eg the (110)) and the (100) to the lesser extent. Consequently, growth is most controlled by the advance of the (11x) plane.

According to the present invention, this problem is overcome by inhibiting or at least strongly reducing the crystal growth in the (001) plane and the (110) and (111) directions.

This can produce waxy fuels having wax crystals of sufficiently small size at low temperatures to pass through filters typically used in diesel engines and heating oil systems and is achieved by the addition of certain additives.

The present invention therefore provides an additive for reducing the size of paraffin wax crystals in a wax containing distillate fuel boiling in the range 120° to 500° C. which crystallises as the fuel is cooled, by propagation of the (001) plane of wax crystal platelets in at least the (11x) direction such that wherein adjacent paraffin wax molecules in said (001) plane intersecting with the (11x) plane are separated by a distance (d), and the dihedral angle between adjacent crystallographic (11x) planes of the wax being θ, said additive containing (i) a bulky group (A and/or B), (ii) a linking group (L) linking the bulky group to (iii) a configurational group (X and Y) which determines the spacing and configuration of (iv) at least two adsorbing groups ($X^1$ and $Y^1$):

(A) wherein the linking group is comprised of two interconnected carbon atoms which join the bulky groups to the configurational groups;

(B) each configurational group is affixed to at least one adsorbing group and a different carbon of the linking group;

(C) said bulky group is capable of exerting a steric effect sufficient to inhibit further wax crysallization subsequent to co-crystallization of the additive with the paraffin wax;

(D) said configurational groups have a structure sufficient to (i) induce each adsorbing group attached thereto to orient with its corresponding intra-molecular adsorbing group at a dihedral angle substantially equal to (θ) (i.e.±10° of θ) and (ii) cause the intra-molecular distance between said adsorbing groups to be within 10% less than and 30% more than (d), whereby said adsorbing groups will occupy positions within the wax crystal lattice parallel to the axis of the paraffin wax chains in the crystal; and (E) said adsorbing groups which may be the same or different are selected from the group consisting of alkyl, alkoxy alkyl, or polyalkoxy alkyl groups containing at least 10 carbon atoms.

Figure 4:
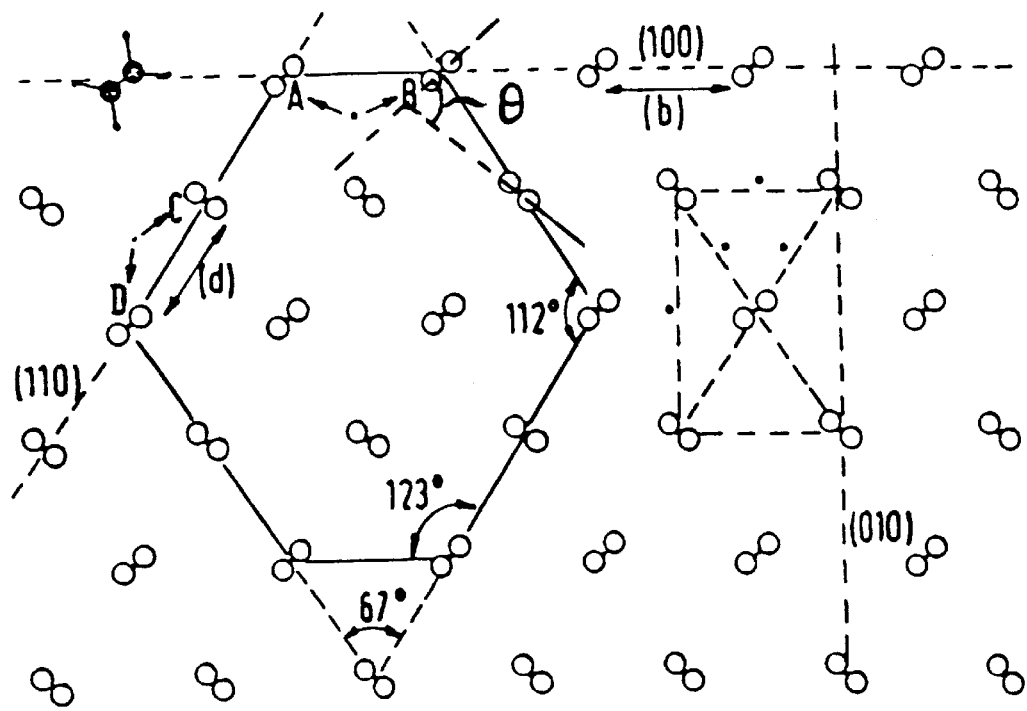
FIG. 4 schematically depicts an enlarged top view of the crystal lattice of a paraffin platelet and includes a schematic illustration of a unit cell.

The occupation of the planes of the crystal is shown in FIG. 4 which is an enlarged top view of the crystal lattice of a paraffin platelet and includes a schematic illustration of a unit cell. The direction of view is the long axis of the paraffin chains. Of each paraffin molecule, only two carbon atoms and four hydrogen atoms (the latter only shown once) can be seen. The other atoms are below the atoms shown, since all carbon atoms of a molecule lie in one molecular symmetry plane. It can be seen from FIG.4 that the distances between two molecules in the (100) plane and the (110) plane, respectively, are virtually the same.

These distances are designated (b) and (d) in FIG. 4., wherein b=4.9 A and d=4.5 A. The main difference between the (100) and the (110) (or more rigorously the (11x) where x is 0 or an integer) planes is the relative orientation of adjacent paraffin molecules. Within the (100) plane, the molecular symmetry planes of single molecules are parallel to each other giving a dihedral angle as shown of $\theta$. In the crystallographic (110) plane, the dihedral angle 0 between the molecular symmetry planes of adjacent wax molecules is about 82°.

According to the invention, the additives will occupy the positions of paraffin molecules which are designated by "C" and "D" in FIG. 4 which may be achieved, for the illustrated wax, if the distance between the substituents is about 4.5 to 5.5 A in an energetically available conformation and the dihedral angle ($\theta'$) between the local symmetry planes of the two adsorbing groups of the additive is about 820, preferably from 75° to 90°.

Thus, the dihedral angle $\theta'$ of the additive adsorbing groups will be controlled to be typically within ±10° preferably within ±5° of the dihedral angle $\theta$ of the wax. It is desireable to have an adsorbing group linked to a configurational group by an ionic bond since this gives more flexibility for the adsorbing groups to attain a dihedral angle close to $\theta$.

A molecule can be modelled by either reading its known atomic co-ordinates into a computer or by building the structure according to the rules of chemical physics with the aid of the computer. Subsequently the structure can be refined by for example:

(a) calculation of the fractional charges on every atom from electronegativity differences (force field method) or quantum mechanical techniques (e.g. CNDO, Q.C.P.E. 141, Indiana University);

(b) optimising the structure using molecular mechanics (compare "Molecular Mechanics", U. Burkert and N. L. Allinger, ACS, 1982);

(c) minimising the overall energy by optimising the conformation, i.e. by rotation around rotating bonds. Care needs to be taken here as the environment on the wax crystal surface is different from that in the gas phase or in solution and it is possible that the additive molecule co-crystallises with the paraffin in a conformation which is not the energetically most favourable conformation in the gas phase. Also allowance must be made for the fact that the additive cannot assume a conformation which is hindered by sterical or electronic factors.

Figure 11:
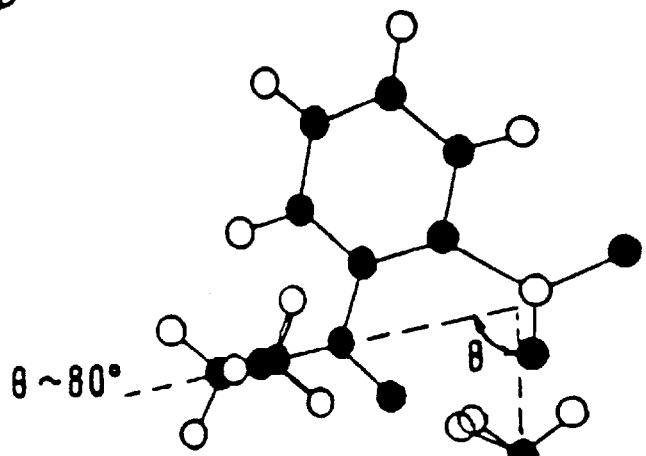
FIG. 11 depicts a molecular model of the N,N-dialkyl ammonium salt of 2-dialkylamide benzene sulphonate prepared in accordance with Example 1.

Using the following criteria, it can be checked whether an additive molecule fits into the (001) plane of the paraffin crystal lattice in the desired positions C and D since:

(1) The intra-molecular distance between the adsorbing groups in the additive molecule must be approximately equal to (i.e. typically from 10% less than to 30% more than, preferably from 8% less than to 20% more than, most preferably from 6% less than to 10% more than) the inter-molecular distance between two adjacent paraffin molecules in the (001) plane intersecting with the (11x) plane, e.g. about 4.5 A. The relative orientation of the adsorbing groups should approximate the arrangement of the n-alkanes in the (110) direction, i.e. the dihedral angle $\theta'$ between the local symmetry planes of the adsorbing groups should be within ±10°, most preferably ±5° of $\theta$ e.g. as illustrated in FIG. 11.

The distance and the angle can be easily measured using the computer programs.

Compounds previously suggested as additives for controlling the size of wax crystals in distillate fuels are certain derivatives of phthalic acid, maleic acid, succinic acid and vinylindene olefins. None of these compounds meet criterium (1) described above. This is illustrated with respect to the following selected examples.

Figure 5:
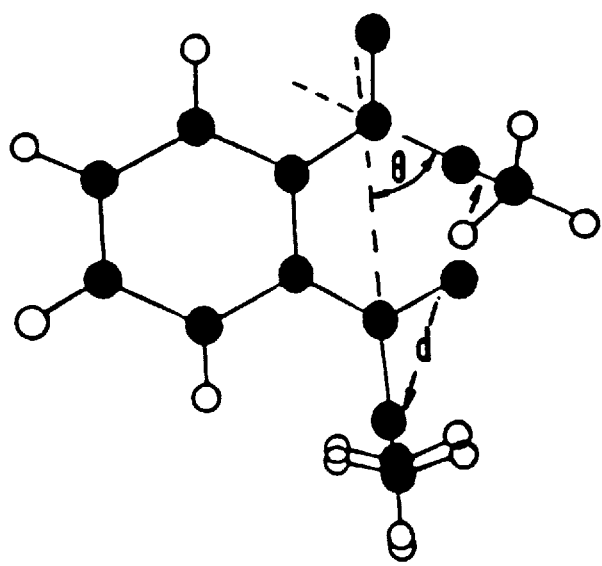
FIG. 5 depicts the conformation of a phthalic diamide.
Figure 6:
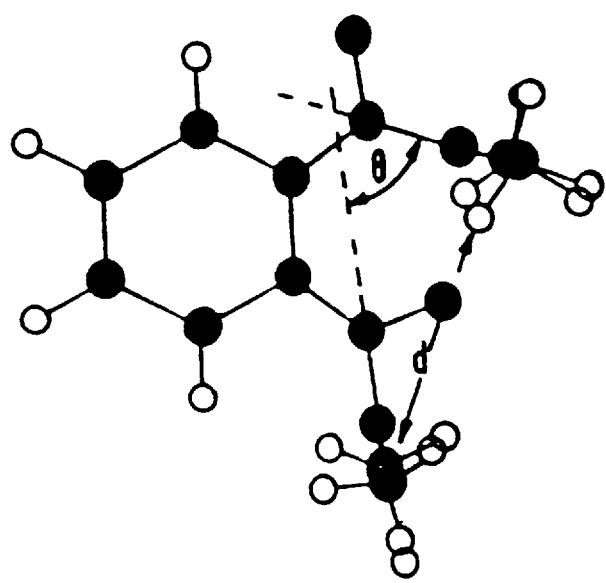
FIG. 6 depicts a distorted conformation of phthalic diamide due to reminimisation.

(a) phthalic diamide in the best case assumes the conformation shown in FIG. 5. in which the intra molecular distance (d) between the adsorbing groups and the dihedral angle $\theta'$ are both too small. The conformation is energetically unfavourable because of sterical hindrance. Reminimisation leads to the distorted conformation shown in FIG. 6.

Figure 7:
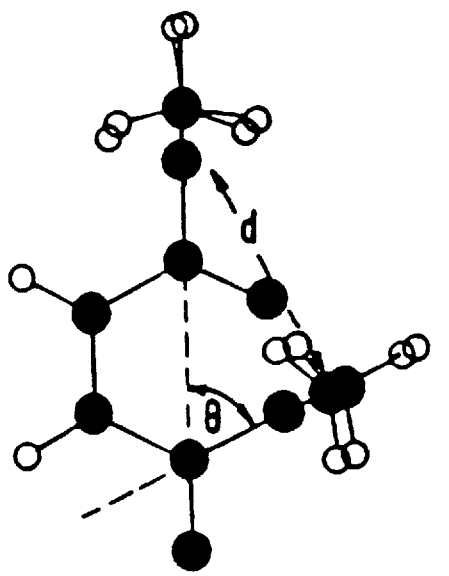
FIG. 7 depicts the conformation of a maleic diamide.
Figure 8:
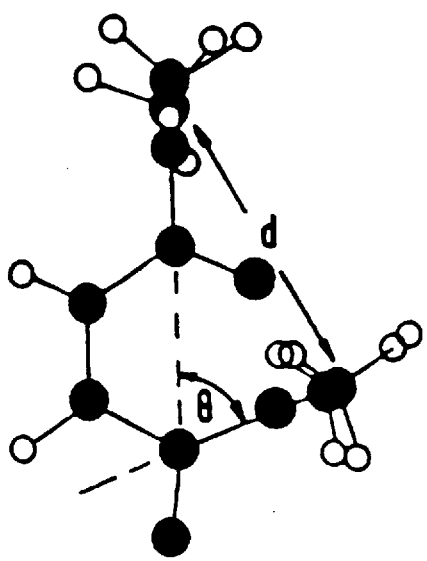
FIG. 8 depicts a distorted conformation of maleic diamine due to reminimisation.

(b) The situation is similar for maleic diamide as can be seen in FIG. 7. Because of steric hindrance reminimisation leads to the distorted conformation of FIG. 8.

Figure 9:
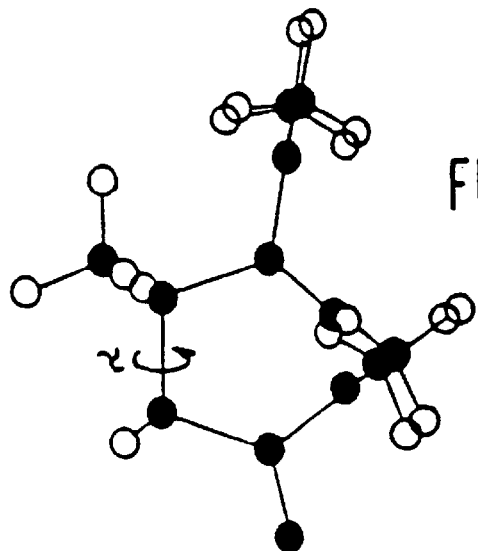
FIG. 9 show that because of steric hindrance succinic acid cannot assume a conformation which comes near to the special arrangement according to the present invention.
Figure 10:
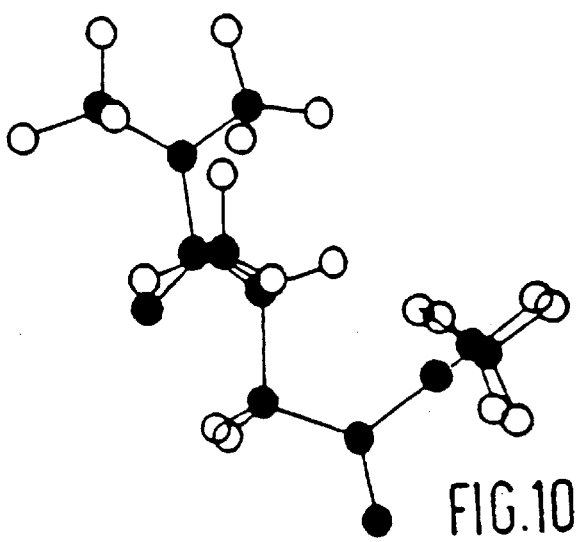
FIG. 10 shows conformation that occurs due to rotation around the C—C single bond the succinic acid.

(c) Because of steric hindrance succinic acid cannot assume a conformation which comes near to the special arrangement according to the invention (compare FIG. 9). By rotation around a C—C single bond the succinic acid switches over to the conformation shown in FIG. 10.

As mentioned, two factors are important in matching of the spacing and configuration of the additive molecule to the wax crystal; firstly, intra-molecular distance of the adsorbing groups of an additive molecule should approximate the separation (i.e. distance) between the n-alkane chains of the wax at the locus of selected wax crystal planes e.g. at the intersection of the (i) (110) and (111) etc. planes or directions and to a lesser extent in the (100) wax crystal plane, and (ii) the (001) wax crystal plane. The adsorbing groups of the additive must occupy the lattice sites (more than one) in positions on the axes at right angles to the axis of the n-alkane chains in the crystal. These separations are in the order of 4.5 to 5.5 A for most paraffin waxes, and the closer the adsorbing groups of the additives are to these distances the more effective the additive.

Secondly, although possibly less important, the relative orientation (conformation) of the adsorbing groups of an additive molecule should preferably approximate the orientation, i.e. $\theta$ of the n-alkanes in the wax crystal.

When the adsorbing groups of the additive match closely the inter-molecular spacings of the n-alkanes in the wax crystal along the (100) and/or (11x) planes where they intersect with the (001) plane and attain conformations which allow the adsorbing groups to orient themselves to similar angles to those of the n-alkanes in the above-mentioned crystal planes, extremely small wax crystals are achieved.

It has been found that these spacings and orientations of the adsorbing groups of the additive molecule can best be achieved by attaching them through appropriate configurational groups to a linking group, e.g. adjacent carbon atoms in a cyclic, or ethylenically unsaturated structure in a cis orientation. The most effective additive is one when at least one configurational group is an —$SO_3(-)$ group.

Desirably, the absorbing groups will contain a carbon or carbon/hetero atom chain of the same order of magnitude as the average carbon chain length in the wax. The wax precipitation from the fuel or oil is generally a range of n-alkanes and hence the reference to the average dimensions. In particular it is preferred that the adsorbing groups are alkyl, alkoxy alkyl or polyalkoxy alkyl groups containing at least 10 chain atoms, $C_{10}$ to $C_{30}$ straight chain alkyl groups being preferred, especially $C_{14}$ to $C_{24}$ most preferably $C_{16}$ to $C_{22}$. For example an absorbing group may be $H_2N^+(C_{18}H_{38})_2$ and the configurational group —$SO_3(-)$. The adsorbing groups of the additives preferably contain alkyl preferably n-alkyl groups which can enable the additive to co-crystallize with the wax. We have found that there should be two or more such groups per molecule and that these should be located on the same side of the additive molecule. Conceptually, the additive molecule can be viewed as having two distinct "sides" joined by the linking group. One "side" will contain the configurational and adsorbing groups and the other "side" will contain a bulky group conveniently made up of a sufficient number of hydrocarbon groups to inhibit further crystallisation e.g. block crystallisation sites or prevent further wax crystallization after the additive molecule has co-crystallized into the n-alkane lattice sites on the wax crystals. The linking group may, structurally constitute part of the bulky group.

The degree of efficiency of the additive is improved as the rate of wax crystallisation decreases. Where fuels are less responsive, efficiency may be improved by blending to adjust the boiling range and the average n-alkane carbon number of the waxes in the fuel.

We have also developed certain novel chemical compounds which fulfil the requirements desired previously.

A further embodiment in the present invention therefore provides a class of novel compounds of the general formula

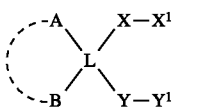
(I)

where

A and B may be the same or different and may be alkyl, alkenyl or aryl;

L is selected from the group consisting of >CH—CH< and >C=C< and A, B and L together can constitute part of a cyclic structure, which can be aromatic, alicyclic or mixed aromatic/alicyclic and with the proviso that when A, B and L do not constitute part of a cyclic structure one of A or B may be hydrogen and in that when L is non-cyclic ethylenic, said $X-X^1$ and $Y-Y^1$ groupings are present in a cis configuration;

X is selected from the group consisting of —$SO_3(-)$ —$S(O_2)O$—, —$S(O_2)$—, —$C(O)$—, —$CO_2^{(-)}$, —$R^4C(O)O$—, —$N(R^3)C(O)$—, —$R^4O$—, —$R^4OC(O)$—, —$R^4$— and —$N(COR^3)$;

when X is —$So_3^{(-)}$ $OR$ —$CO_2^{(-)}$ $X^1$ is selected from the group consisting of $N^{(+)}R_3^3R^1$, $N^{(+)}HR_2^3R^1$, $N^{(+)}H_2 R^3R^1$ and $N^{(+)}H_3R^1$;

when X is —$S(O_2)$— or —$C(O)$—

$X^1$ is —$NR^3R^1$;

when X is —$S(O_2)O$—, —$R^4C(O)O$—, —$N(R^3)C(O)$—, —$R^4O$—, —$R^4OC(O)$—, —$R^4$— and —$N(COR3)$—

$X^1$ is—$R^1$;

Y is selected from —$SO_3^{(-)}$, —$S(O_2)$— or —$S(O_2)O$—;

when Y is —$SO_3^{(-)}$ $Y^1$ is selected from the group consisting of $N^{(+)}R_3^3R^2$, $N^{(+)}HR_2^3R^2$, $N^{(+)}H_2R^3R^2$ and $N^{(+)}H_3R^2$;

when Y is —$S(O_2)$—

$Y^1$ is —$NR^3R^2$;

when Y is —$S(O_2)O$—

$Y^1$ is —$R^2$;

and wherein $R^1$ and $R^2$ are independently selected from the group consisting of alkyl typically $C_{10}$ to $C_{40}$ alkyl more preferably $C_{10}$ to $C_{30}$ more preferably $C_{14}$ to $C_{24}$ alkyl, alkoxy alkyl or polyalkoxyalkyl groups containing at least 10 typically ten to 40 carbon atoms in their main chain $R^3$ is hydrocarbyl preferably alkyl, more preferably $C_1$ to $C_{30}$ most preferably $C_{10}$ to $C_{30}$ straight chain alkyl and each $R^3$ may be the same or different and $R^4$ is —$(CH_2)n$ where n is from 0 to 5.

It is preferred that $X^1$ and $Y^1$ together contain at least three alkyl, alkoxy alkyl or polyalkoxy alkyl groups.

In these compounds A and B together or separately form one or more bulky groups, L is the linking group which may also be part of the bulky group, X and/or Y are configurational groups and $X^1$ and/or $Y^1$ constitute the adsorbing groups.

When L is part of a cyclic structure together with A and B, the cyclic structure may be aromatic, alicyclic, or mixed aromatic/alicyclic. More specifically the cyclic structure may be mono-cyclic or polycyclic aromatic, polynuclear aromatic, heteroaromatic, and heteroalicyclic. The ring structure may be saturated or unsaturated with one or more unsaturations; with at least one ring containing 4 or more atoms, and it may be multicyclic, bridged and may be substituted. When the cyclic structure is heterocyclic it may include one or more of N, S or O atoms.

Examples of suitable monocyclic ring structures are benzene, cyclohexane, cyclohexene, cyclopentane, pyridine and furan. The ring structure may contain additional substituents.

Suitable polycyclic compounds, that is those having two or more ring structures, can take various forms. They can be (a) fused aromatic structures, (b) fused partially hydrogenated aromatic ring structures where at least one but not all rings are aromatic, (c) alicyclic which includes fused alicyclic, bridged alicyclic, spiro alicyclic compounds (d) hydrocarbon ring assemblies of like or unlike rings which may be aromatic, alicyclic or mixed; (e) any of (a) to (d) which contain at least one hetero atom.

Fused aromatic structures from which the compounds defined by L, A and B collectively may be derived include for example naphthalene, anthracene, phenathrene, fluorene, pyrene and indene. Suitable condensed ring structures where none or not all rings are benzene include for example azulene, hydronaphthalene, hydroindene, hydrofluorene, diphenylene. Suitable bridged alicyclic structures include bicycloheptane and bicycloheptene.

Suitable ring assemblies include biphenyl and cyclohexyl benzene.

Suitable heteropolycyclic structures include quinuclidine and indole.

Suitable heterocyclic compounds defined by L, A and B collectively from which the compounds of this invention may be derived include quinoline; indole, 2,3 dihydroindole, benzofuran, coumarin and isocoumarin, benzothiophene, carbazole and thiodiphenylamine.

Suitable non-aromatic or partially saturated ring systems defined by L, A and B collectively include decalin (decahydronaphthalene), α- pinene, cadinene, bornylene. Suitable bridged compounds include norbornene, bicycloheptane (norbornane), bicyclo octane and bicyclo octene.

When L, A and B form part of a cyclic structure X and Y are preferably attached to adjoining ring atoms located completely within a single ring whether mono- or polycyclic. For example if one were to use naphthalene, these substituents could not be attached to the 1,8- or 4,5-positions, but would have to be attached to the 1,2-, 2,3-, 3,4-, 5,6-, 6,7- or 7,8- positions.

The hydrogen- and carbon-containing groups in the substituents A and B when L is ethylenic and not part of a ring with A and B, are preferably alkyl, typically $C_1$ to $C_{24}$ alkyl or alkenyl, aryl typically $C_6$ to $C_{14}$ aryl. Such groups may also be halogenated preferably only containing a small proportion of halogen atoms (e.g. chlorine atoms), for example less than 20 weight per cent. The A and B groups are preferably aliphatic, e.g. alkylene. They are preferably straight chain. Unsaturated hydrocarbyl groups, e.g. alkenyl, could be used but they are not preferred.

When the compounds are used as distillate fuel additives we prefer that $R^1$, $R^2$, and $R^3$ when present contain 10 to 24 carbon atoms, for example 14 to 22 preferably 18 to 22 carbon atoms and are preferably straight chain or branched at the 1 or 2 position. Suitable alkyl groups include decyl, dodecyl, tetradecyl, eicosyl and docosyl (behenyl). Alternatively the groups may be polyethylene oxide or polypropylene oxide, the main chain of the groups being the longest linear segment.

The especially preferred compounds defined by formula I are the amides or amine salts of secondary amines. Although two substituents are necessary for the cyclic derivatives described above it should be realised that these cyclic compounds can contain one or more further substituents attached to ring atoms of the cyclic compounds.

The compounds of the present invention may be prepared from a reactant such as

(II)

where A, B, L are as previously defined and $X^2$ and $Y^2$ are as defined in connection with X and Y and additionally $X^2$ and $Y^2$ together can form part of a cyclic anhydride structure wherein an oxy group (>O) is common to both $X^2$ and $Y^2$.

Preferred reactants are those in which $X^2$ is selected from —C(O)O— and $Y^2$ is —SO$_3$(-) and particularly preferred reactants are compounds of the formula:

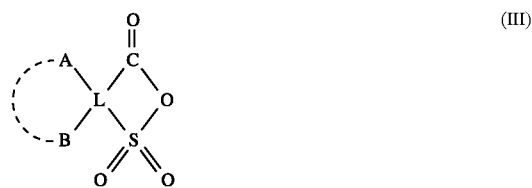
(III)

The most preferred reactants are compounds in which A, B and L together are part of a cyclic structure especially an aromatic ring. A particularly preferred reactant is represented by the formula:

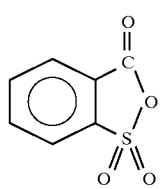
(IV)

in which the aromatic ring may be substituted, and in which the aromatic ring represents A, B and L collectively, and $X^2$ and $Y^2$ in formula II together form an anhydride ring as in formula III.

The compounds of the present invention are prepared by reacting both the $Y^2$-H group and the $X^2$-H group with amines, alcohols, quaternary ammonium salts etc or mixtures thereof. Where the final compounds are the amides or amine salts they are preferably of a secondary amine which has a hydrogen and carbon containing group containing at least 10 carbon atoms preferably a straight chain alkyl group containing from 10 to 30 more preferably 16 to 24 carbon atoms. Such amides or salts may be prepared by reacting the acid or anhydride with a secondary amine or alternatively by reaction with an amine derivative. Removal of water and heating are generally necessary to prepare the amides from the acids. Alternatively the $Y^2$-H and $X^2$-H groups may be reacted with an alcohol containing at least 10 carbon atoms or a mixture of an alcohol and an amine or sequentially with an amine and an alcohol or vice-versa.

Thus, the final additive compounds, comprise as a result of the identity of X–$X^1$, and Y–$Y^1$ esters, amides, ethers, primary, secondary or tertiary amine salts, amino amides, amino ethers and the like.

The preferred compounds of the present invention are of the formulae:

(V)

more preferably

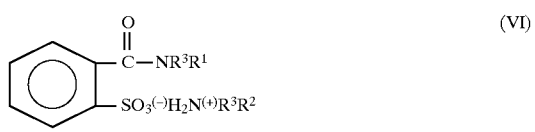
(VI)

and

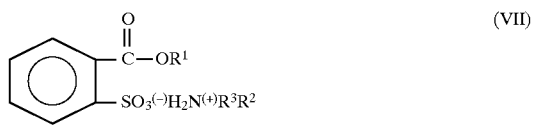
(VII)

Illustrative preferred additives are shown in chart form in Table 1.

TABLE 1

| A B L | X—X¹ | Y—Y¹ | R¹, R² | R³ |
|---|---|---|---|---|
|  | —C(O)—NR³R¹ | —SO₃(-)(+)H₃NR² | $C_{18}H_{38}$ | $C_{20}H_{42}$ |
| " | " | " | " | $C_{16}H_{34}$ |
| " | " | " | " | $C_{18}H_{38}$ |
| " | " | " | $C_{20}H_{42}$ | $C_{20}H_{42}$ |
| " | " | " | " | $C_{16}H_{34}$ |
| " | " | " | " | $C_{18}H_{38}$ |
| " | " | —SO₂—OR² | $C_{18}H_{38}$ | $C_{20}H_{42}$ |
| " | " | " | " | $C_{16}H_{34}$ |
| " | " | " | " | $C_{18}H_{38}$ |
|  | " | " | $C_{20}H_{42}$ | $C_{20}H_{42}$ |
| " | " | " | " | $C_{16}H_{34}$ |
| " | " | " | " | $C_{18}H_{38}$ |
| " | " | —SO₂—NR³R² | $C_{18}H_{38}$ | $C_{20}H_{42}$ |
| " | " | " | " | $C_{16}H_{34}$ |
| " | " | " | " | $C_{18}H_{38}$ |
| " | " | " | $C_{20}H_{42}$ | $C_{20}H_{42}$ |
| " | " | " | " | $C_{16}H_{34}$ |
| " | " | " | " | $C_{18}H_{38}$ |
| " | " | —SO₂—OR² | $C_{18}H_{38}$ | $C_{20}H_{42}$ |
| " | " | " | " | $C_{16}H_{34}$ |
| " | " | " | " | $C_{18}H_{38}$ |
|  | " | " | $C_{20}H_{42}$ | $C_{20}H_{42}$ |
| " | " | " | " | $C_{16}H_{34}$ |
| " | " | " | " | $C_{18}H_{38}$ |
| " | " | —SO₃(-)(+)NR₃³R² | $C_{18}H_{38}$ | $C_{20}H_{42}$ |
| " | " | " | " | $C_{16}H_{34}$ |
| " | " | " | " | $C_{18}H_{38}$ |
| " | " | " | $C_{20}H_{42}$ | $C_{20}H_{42}$ |
| " | " | " | " | $C_{16}H_{34}$ |
| " | " | " | " | $C_{18}H_{38}$ |
| " | " | —SO₃(-)(+)NR₂⁸R² | $C_{18}H_{38}$ | $C_{20}H_{42}$ |
| " | " | " | " | $C_{16}H_{34}$ |
| " | " | " | " | $C_{18}H_{38}$ |
|  | " | " | $C_{20}H_{42}$ | $C_{20}H_{42}$ |
| " | " | " | " | $C_{16}H_{34}$ |
| " | " | " | " | $C_{18}H_{38}$ |
| " | —C(O)—OR² | —SO₃(-)(+)H₃NR² | $C_{18}H_{38}$ | " |
| " | " | " | " | " |
| " | " | " | $C_{20}H_{42}$ | " |
| " | " | " | " | " |
| " | " | —SO₂—OR² | $C_{18}H_{38}$ | " |
| " | " | " | " | " |
| " | " | " | $C_{20}H_{42}$ | " |

TABLE 1-continued $$\begin{array}{c} \phantom{-}A \diagdown \phantom{L} \diagup X-X^1 \\ \phantom{-}\phantom{A}\phantom{B}L \\ \phantom{-}B \diagup \phantom{L} \diagdown Y-Y^1 \end{array}$$

| A B L | X—X¹ | Y—Y¹ | R¹, R² | R³ |
|---|---|---|---|---|
| " | " | " | " | |
| " | " | $-SO_2-NR^3R^2$ | $C_{18}H_{38}$ | $C_{20}H_{42}$ |
| " | " | " | " | $C_{16}H_{34}$ |
| " | " | " | " | $C_{18}H_{38}$ |
| " | " | " | $C_{20}H_{42}$ | $C_{20}H_{42}$ |
| " | " | " | " | $C_{16}H_{34}$ |
| " | " | " | " | $C_{18}H_{38}$ |
| " | " | $-SO_2-OR^2$ | $C_{18}H_{38}$ | |
| " | " | " | " | |
|  | " | " | $C_{20}H_{42}$ | |
| " | " | " | " | |
| " | " | $-SO_3(-)(+)NR_3^3R^2$ | $C_{18}H_{38}$ | |
| " | " | " | " | $C_{16}H_{34}$ |
| " | " | " | " | $C_{18}H_{48}$ |
| " | " | " | $C_{20}H_{42}$ | $C_{20}H_{42}$ |
| " | " | " | " | $C_{16}H_{34}$ |
| " | " | " | " | $C_{18}H_{48}$ |
| " | " | $-SO(-)(+)NHR_2^3R^2$ | $C_{18}H_{38}$ | $C_{20}H_{42}$ |
| " | " | " | " | $C_{16}H_{34}$ |
| " | " | " | " | $C_{18}H_{38}$ |
|  | " | " | $C_{20}H_{42}$ | $C_{20}H_{42}$ |
| " | " | " | " | $C_{16}H_{34}$ |
| " | " | " | " | $C_{18}H_{38}$ |
| " | $-N(R^3)C(O)-R^1$ | $-SO_3(-)(+)H_3R^2$ | $C_{18}H_{38}$ | |
| " | " | " | " | |
| " | " | " | $C_{20}H_{42}$ | |
| " | " | " | " | |
| " | " | $-SO_2-OR^2$ | $C_{18}H_{38}$ | |
| " | " | " | " | |
|  | " | " | $C_{20}H_{42}$ | |
| " | " | " | " | |
| " | " | $-SO_2-NR^3R^2$ | $C_{18}H_{38}$ | $C_{20}H_{42}$ |
| " | " | " | " | $C_{16}H_{34}$ |
| " | " | " | " | $C_{18}H_{38}$ |
| " | " | " | $C_{20}H_{42}$ | $C_{20}H_{42}$ |
| " | " | " | " | $C_{16}H_{34}$ |
| " | " | " | " | $C_{18}H_{38}$ |
| " | " | $-SO_2-OR^2$ | $C_{18}H_{38}$ | |
| " | " | " | " | |
|  | " | " | $C_{20}H_{42}$ | |
| " | " | " | " | |

TABLE 1-continued

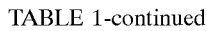

| A | B | L | X—X¹ | Y—Y¹ | R¹, R² | R³ |
|---|---|---|------|------|--------|-----|
| " | " | " | " | —SO₃(-)(+)NR₃³R² | C₁₈H₃₈ | C₂₀H₄₂ |
|   |   |   |   |   | " | C₁₆H₃₄ |
|   |   |   |   |   |   | C₁₈H₃₈ |
|   |   |   |   |   | C₂₀H₄₂ | C₂₀H₄₂ |
|   |   |   |   |   | " | C₁₆H₃₄ |
|   |   |   |   |   |   | C₁₈H₃₈ |
| " | " | " | " | —SO(-)(+)NHR₂³R² | C₁₈H₃₈ | C₂₀H₄₂ |
|   |   |   |   |   | " | C₁₆H₃₄ |
|   |   |   |   |   |   | C₁₈H₃₈ |
| phenyl | | " | " | " | C₂₀H₄₂ | C₂₀H₄₂ |
| " | " | " | " | " | " | C₁₆H₃₄ |
|   |   |   |   |   |   | C₁₈H₃₈ |
| " | " | " | —C(O)—NR³R¹ | —SO₃(-)(+)H₃NR² | C₁₈H₃₈ | C₂₀H₄₂ |
|   |   |   |   |   | " | C₁₆H₃₄ |
|   |   |   |   |   |   | C₁₈H₃₈ |
|   |   |   |   |   | C₂₀H₄₂ | C₂₀H₄₂ |
|   |   |   |   |   | " | C₁₆H₃₄ |
|   |   |   |   |   |   | C₁₈H₃₈ |
| " | " | " | " | —SO₂—OR² | C₁₈H₃₈ | C₂₀H₄₂ |
|   |   |   |   |   | " | C₁₆H₃₄ |
|   |   |   |   |   |   | C₁₈H₃₈ |
| phenyl | | " | " | " | C₂₀H₄₂ | C₂₀H₄₂ |
| " | " | " | " | " | " | C₁₆H₃₄ |
|   |   |   |   |   |   | C₁₈H₃₈ |
| " | " | " | " | —SO₂—NR³R² | C₁₈H₃₈ | C₂₀H₄₂ |
|   |   |   |   |   | " | C₁₆H₃₄ |
|   |   |   |   |   |   | C₁₈H₃₈ |
|   |   |   |   |   | C₂₀H₄₂ | C₂₀H₄₂ |
|   |   |   |   |   | " | C₁₆H₃₄ |
|   |   |   |   |   |   | C₁₈H₃₈ |
| " | " | " | " | —SO₂—OR² | C₁₈H₃₈ | C₂₀H₄₂ |
|   |   |   |   |   | " | C₁₆H₃₄ |
|   |   |   |   |   |   | C₁₈H₃₈ |
| phenyl | | " | " | " | C₂₀H₄₂ | C₂₀H₄₂ |
| " | " | " | " | " | " | C₁₆H₃₄ |
|   |   |   |   |   |   | C₁₈H₃₈ |
| " | " | " | " | —SO₃(-)(+)NR₃³R² | C₁₈H₃₈ | C₂₀H₄₂ |
|   |   |   |   |   | " | C₁₆H₃₄ |
|   |   |   |   |   |   | C₁₈H₃₈ |
|   |   |   |   |   | C₂₀H₄₂ | C₂₀H₄₂ |
|   |   |   |   |   | " | C₁₆H₃₄ |
|   |   |   |   |   |   | C₁₈H₃₈ |
| " | " | " | " | —SO₃(-)(+)NHR₂³R² | C₁₈H₃₈ | C₂₀H₄₂ |
|   |   |   |   |   | " | C₁₆H₃₄ |
|   |   |   |   |   |   | C₁₈H₃₈ |
| phenyl | | " | " | " | C₂₀H₄₂ | C₂₀H₄₂ |
| " | " | " | " | " | " | C₁₆H₃₄ |
|   |   |   |   |   |   | C₁₈H₃₈ |
| " | " | " | —SO₃(-)(+)NR₃³R¹ | —SO₃(-)(+)H₃NR² | C₁₈H₃₈ | C₂₀H₄₂ |

TABLE 1-continued

| A B L | X—X¹ | Y—Y¹ | R¹, R² | R³ |
|---|---|---|---|---|
| " | " | " | " | $C_{16}H_{34}$ |
| " | " | " | " | $C_{18}H_{38}$ |
| " | " | " | $C_{20}H_{42}$ | $C_{20}H_{42}$ |
| " | " | " | " | $C_{16}H_{34}$ |
| " | " | " | " | $C_{18}H_{38}$ |
| " | " | $-SO_2-OR^2$ | $C_{18}H_{38}$ | $C_{20}H_{42}$ |
| " | " | " | " | $C_{16}H_{34}$ |
| " | " | " | " | $C_{18}H_{38}$ |
|  | " | " | $C_{20}H_{42}$ | $C_{20}H_{42}$ |
| " | " | " | " | $C_{16}H_{34}$ |
| " | " | " | " | $C_{18}H_{38}$ |
| " | " | $-SO_2-NR^3R^2$ | $C_{18}H_{38}$ | $C_{20}H_{42}$ |
| " | " | " | " | $C_{16}H_{34}$ |
| " | " | " | " | $C_{18}H_{38}$ |
| " | " | " | $C_{20}H_{42}$ | $C_{20}H_{42}$ |
| " | " | " | " | $C_{16}H_{34}$ |
| " | " | " | " | $C_{18}H_{38}$ |
| " | " | $-SO_2-OR_2$ | $C_{18}H_{38}$ | $C_{20}H_{42}$ |
| " | " | " | " | $C_{16}H_{34}$ |
| " | " | " | " | $C_{18}H_{38}$ |
|  | " | " | $C_{20}H_{42}$ | $C_{20}H_{42}$ |
| " | " | " | " | $C_{16}H_{34}$ |
| " | " | " | " | $C_{18}H_{38}$ |
| " | " | $-SO_3(-)(+)NR_3^3R^2$ | $C_{18}H_{38}$ | $C_{20}H_{42}$ |
| " | " | " | " | $C_{16}H_{34}$ |
| " | " | " | " | $C_{18}H_{38}$ |
| " | " | " | $C_{20}H_{42}$ | $C_{20}H_{42}$ |
| " | " | " | " | $C_{16}H_{34}$ |
| " | " | " | " | $C_{18}H_{38}$ |
| " | " | $-SO_3(-)(+)NHR_2^3R^2$ | $C_{18}H_{38}$ | $C_{20}H_{42}$ |
| " | " | " | " | $C_{16}H_{34}$ |
| " | " | " | " | $C_{18}H_{38}$ |
|  | " | " | $C_{20}H_{42}$ | $C_{20}H_{42}$ |
| " | " | " | " | $C_{16}H_{34}$ |
| " | " | " | " | $C_{18}H_{38}$ |
| " | $-R^4-C(O)OR^1$ | $-SO_3(-)(+)H_3NR^2$ | $C_{18}H_{38}$ | $C_{20}H_{42}$ |
| " | " | " | " | $C_{16}H_{34}$ |
| " | " | " | " | $C_{18}H_{38}$ |
| " | " | " | $C_{20}H_{42}$ | $C_{20}H_{42}$ |
| " | " | " | " | $C_{16}H_{34}$ |
| " | " | " | " | $C_{18}H_{38}$ |
| " | " | $-SO_2-OR^2$ | $C_{18}H_{38}$ | $C_{20}H_{42}$ |
| " | " | " | " | $C_{16}H_{34}$ |
| " | " | " | " | $C_{18}H_{38}$ |
|  | " | " | $C_{20}H_{42}$ | $C_{20}H_{42}$ |
| " | " | " | " | $C_{16}H_{34}$ |
| " | " | " | " | $C_{18}H_{38}$ |
| " | " | $-SO_2-NR^3R^2$ | $C_{18}H_{38}$ | $C_{20}H_{42}$ |
| " | " | " | " | $C_{16}H_{34}$ |
| " | " | " | " | $C_{18}H_{38}$ |

TABLE 1-continued

| A B L | X—X¹ | Y—Y¹ | R¹, R² | R³ |
|---|---|---|---|---|
| " | " | " | C₂₀H₄₂ | C₂₀H₄₂ |
| " | " | " | " | C₁₆H₃₄ |
| " | " | " | " | C₁₈H₃₈ |
| " | " | —SO₂—OR² | C₁₈H₃₈ | C₂₀H₄₂ |
| " | " | " | " | C₁₆H₃₄ |
| " | " | " | " | C₁₈H₃₈ |
| (benzene) | " | " | C₂₀H₄₂ | C₂₀H₄₂ |
| " | " | " | " | C₁₆H₃₄ |
| " | " | " | " | C₁₈H₃₈ |
| " | " | —SO₃(−)(+)NR₃³R² | C₁₈H₃₈ | C₂₀H₄₂ |
| " | " | " | " | C₁₆H₃₄ |
| " | " | " | " | C₁₈H₃₈ |
| " | " | " | C₂₀H₄₂ | C₂₀H₄₂ |
| " | " | " | " | C₁₆H₃₄ |
| " | " | " | " | C₁₈H₃₈ |
| " | " | —SO₃(−)(+)NHR₂³R² | C₁₈H₃₈ | C₂₀H₄₂ |
| " | " | " | " | C₁₆H₃₄ |
| " | " | " | " | C₁₈H₃₈ |
| (benzene) | " | " | C₂₀H₄₂ | C₂₀H₄₂ |
| " | " | " | " | C₁₆H₃₄ |
| " | " | " | " | C₁₈H₃₈ |
| " | —R⁴—O—R³ | —SO₃(−)(+)H₂NR² | C₁₈H₃₈ | C₂₀H₄₂ |
| " | " | " | " | C₁₆H₃₄ |
| " | " | " | " | C₁₈H₃₈ |
| " | " | " | C₂₀H₄₂ | C₂₀H₄₂ |
| " | " | " | " | C₁₆H₃₄ |
| " | " | " | " | C₁₈H₃₈ |
| " | " | —SO₂—OR² | C₁₈H₃₈ | C₂₀H₄₂ |
| " | " | " | " | C₁₆H₃₄ |
| " | " | " | " | C₁₈H₃₈ |
| (benzene) | " | " | C₂₀H₄₂ | C₂₀H₄₂ |
| " | " | " | " | C₁₆H₃₄ |
| " | " | " | " | C₁₈H₃₈ |
| " | " | —SO₂—NR³R² | C₁₈H₃₈ | C₂₀H₄₂ |
| " | " | " | " | C₁₆H₃₄ |
| " | " | " | " | C₁₈H₃₈ |
| " | " | " | C₂₀H₄₂ | C₂₀H₄₂ |
| " | " | " | " | C₁₆H₃₄ |
| " | " | " | " | C₁₈H₃₈ |
| " | " | —SO₂—OR² | C₁₈H₃₈ | C₂₀H₄₂ |
| " | " | " | " | C₁₆H₃₄ |
| " | " | " | " | C₁₈H₃₈ |
| (benzene) | " | " | C₂₀H₄₂ | C₂₀H₄₂ |
| " | " | " | " | C₁₆H₃₄ |
| " | " | " | " | C₁₈H₃₈ |
| " | " | —SO₃(−)(+)NR³R₃² | C₁₈H₃₈ | C₂₀H₄₂ |
| " | " | " | " | C₁₆H₃₄ |
| " | " | " | " | C₁₈H₃₈ |
| " | " | " | C₂₀H₄₂ | C₂₀H₄₂ |
| " | " | " | " | C₁₆H₃₄ |

TABLE 1-continued

| A | B | L | X—X¹ | Y—Y¹ | R¹, R² | R³ |
|---|---|---|------|------|--------|-----|
| " | " | " | " | " | " | $C_{18}H_{38}$ |
| " | " | " | " | $-SO_{3(-)(+)NHR^3R_2^2}$ | $C_{18}H_{38}$ | $C_{20}H_{42}$ |
| " | " | " | " | " | " | $C_{16}H_{34}$ |
| " | " | " | " | " | " | $C_{18}H_{38}$ |
|  | | " | " | " | $C_{20}H_{42}$ | $C_{20}H_{42}$ |
| " | " | " | " | " | " | $C_{16}H_{34}$ |
| " | " | " | " | " | " | $C_{18}H_{38}$ |
| " | " | " | $-R^4-O-R^1$ | $-SO_{2(-)(+)H3}NR^2$ | $C_{18}H_{38}$ | $C_{20}H_{42}$ |
| " | " | " | " | " | " | $C_{16}H_{34}$ |
| " | " | " | " | " | " | $C_{18}H_{38}$ |
| " | " | " | " | " | $C_{20}H_{42}$ | $C_{20}H_{42}$ |
| " | " | " | " | " | " | $C_{16}H_{34}$ |
| " | " | " | " | " | " | $C_{18}H_{38}$ |
| " | " | " | " | $-SO_2-OR^2$ | $C_{18}H_{38}$ | $C_{20}H_{42}$ |
| " | " | " | " | " | " | $C_{16}H_{34}$ |
| " | " | " | " | " | " | $C_{18}H_{38}$ |
|  | | " | " | " | $C_{20}H_{42}$ | $C_{20}H_{42}$ |
| " | " | " | " | " | " | $C_{16}H_{34}$ |
| " | " | " | " | " | " | $C_{18}H_{38}$ |
| " | " | " | " | $-SO_2-NR^3R^2$ | $C_{18}H_{38}$ | $C_{20}H_{42}$ |
| " | " | " | " | " | " | $C_{16}H_{34}$ |
| " | " | " | " | " | " | $C_{18}H_{38}$ |
| " | " | " | " | " | $C_{20}H_{42}$ | $C_{20}H_{42}$ |
| " | " | " | " | " | " | $C_{16}H_{34}$ |
| " | " | " | " | " | " | $C_{18}H_{38}$ |
| " | " | " | " | $-SO_2-OR^2$ | $C_{18}H_{38}$ | $C_{20}H_{42}$ |
| " | " | " | " | " | " | $C_{16}H_{34}$ |
| " | " | " | " | " | " | $C_{18}H_{38}$ |
|  | | " | " | " | $C_{20}H_{42}$ | $C_{20}H_{42}$ |
| " | " | " | " | " | " | $C_{16}H_{34}$ |
| " | " | " | " | " | " | $C_{18}H_{38}$ |
| " | " | " | " | $-SO_3(-)(+)NR_3^3R^2$ | $C_{18}H_{38}$ | $C_{20}H_{42}$ |
| " | " | " | " | " | " | $C_{16}H_{34}$ |
| " | " | " | " | " | " | $C_{18}H_{38}$ |
| " | " | " | " | " | $C_{20}H_{42}$ | $C_{20}H_{42}$ |
| " | " | " | " | " | " | $C_{16}H_{34}$ |
| " | " | " | " | " | " | $C_{18}H_{38}$ |
| " | " | " | " | $-SO_3(-)(+)NHR_2^3R^2$ | $C_{18}H_{38}$ | $C_{20}H_{42}$ |
| " | " | " | " | " | " | $C_{16}H_{34}$ |
| " | " | " | " | " | " | $C_{18}H_{38}$ |
|  | | " | " | " | $C_{20}H_{42}$ | $C_{20}H_{42}$ |
| " | " | " | " | " | " | $C_{16}H_{34}$ |
| " | " | " | " | " | " | $C_{18}H_{38}$ |

Where $R^4$ is present it may be $CH_2$, $(CH_2)_2$ or $(CH_2)_3$.

Alternatives for A, B and L are:

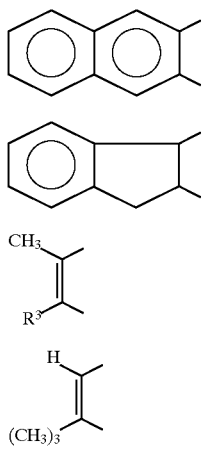

We have found that by using the novel compounds of the present invention as additives for distillate fuels the wax crystals which form as the fuel cools are sufficiently small to pass through the filters of typical diesel engines and heating systems rather than forming a cake on the filter.

Fuels with such small crystals are novel and of great benefit and according to a further aspect of this invention provides additive treated distillate fuel oil boiling in the range 120° C. to 500° C. and which has a wax content of at least 0.5 wt. % and preferably at least 0.3 wt. % at a temperature of 10° C. below the wax appearance temperature, to produce wax crystals at that temperature having an average particle size less than 4000 nanometres 3,000 nanometres, sometimes less than 2000 nanometres and depending on the fuel, the crystals can be of average particle size less than 1500 or preferably 1000 nanometres.

We have also found that this reduction of wax crystal size according to the invention reduces the tendency of the wax crystals to settle in the fuel during storage and can also result in a further improvement in the CFPP performance of the fuel.

The Wax Appearance Temperature (WAT) of the fuel is measured by differential scanning calorimetry (DSC). In this test a small sample of fuel (25 ul) is cooled at 2° C./minute together with a reference sample of similar thermal capacity but which will not precipitate wax in the temperature range of interest (such as kerosene). An exotherm is observed when crystallisation commences in the sample. For example the WAT of the fuel may be measured by the extrapolation technique on the Mettler TA 2000B.

The wax content is derived from the DSC trace by integrating the area enclosed by the baseline and the exotherm down to the specified temperature. The calibration having been previously performed on a known amount of crystallizing wax.

The wax crystal average particle size is measured by analysing a Scanning Electron Micrograph of a fuel sample at a magnification of 4000 to 8000 X and measuring the longest axis of 50 crystals over a predetermined grid. We find that providing the average size is less than 4000 nanometres the wax will begin to pass through the typical paper filters used in diesel engines together with the fuel although we prefer that the size be below 3000 nanometres, more preferably below 2000 and most preferably below 1000 nanometres, the actual size attainable depends upon the original nature of the fuel and the nature and amount of additive used but we have found that these sizes and smaller are attainable.

The ability to obtain such small wax crystals in the fuel shows significant benefit in diesel engine operability as shown by pumping fuel previously stirred to remove settled wax effects through a diesel filter at from 8 to 15 ml/second and 1.0 to 2.4 litres per minute per square metre of filter surface area at a temperature at least 5° C. below the wax appearance temperature with at least 1 wt. % of the fuel being present in the form of solid wax.

Both fuel and wax are considered to successfully pass through the filter if one or more of the following criteria are satisfied:

(i) When 18 to 20 litres of fuel have passed through the filter the pressure drop across the filter does not exceed 50 KPa, preferably 25 KPa, more preferably 10 KPa, most preferably 5 KPa.

(ii) At least 60%, preferably at least 80%, more preferably at least 90 wt. % of the wax present in the fuel, as determined by the DSC test is found to be present in the fuel leaving the filter.

(iii) Whilst pumping 18 to 20 litres of fuel through the filter, the flow rate always remains at above 60% of the initial flow rate and preferably above 80%.

These fuels have outstanding benefits compared to previous distillate fuels improved in their cold flow properties by the addition of conventional additives. For example the fuels are operable at temperatures approaching the pour point and not restricted by the inability to pass the CFPP test. Hence these fuels either pass the CFPP test at significantly lower temperatures or obviate the need to pass that test. The fuels also have improved cold start performance at low temperatures since they do not rely on recirculation of warm fuel to dissolve undesirable wax deposits. The fuels also have a reduced tendency for the wax crystals to settle in the fuel during storage reducing the tendency for wax to agglomerate at the bottom of storage vessels so blocking filters, etc.

The small crystals may be obtained by adding the compounds of the invention and the amount of the compound added to the distillate fuel oil is preferably 0.001 to 0.5 wt. %, for example 0.01 to 0.10 wt. % based on the weight of fuel.

The compound may conveniently be dissolved in a suitable solvent to form a concentrate of from 20 to 90, e.g. 30 to 80 weight % in the solvent. Suitable solvents include kerosene, aromatic naphthas, mineral lubricating oils etc.

The best effect is usually obtained when the compounds of the invention are used in combination with other additives known for improving the cold flow properties of distillate fuels generally, although they may be used on their own.

The compounds are preferably used together with what are known as comb polymers of the general formula

where D=R, C(O).OR, OC(O).R, R'C(O).OR or OR
E=H or $CH_3$ or D or R'
G=H, or D
m=1.0 (homopolymer) to 0.4 (mole ratio)
J=H, R', Aryl or Heterocyclic group, R'CO.OR
K=H, C(O).OR', OC(O).R', OR', C(O)OH
L=H, R', C(O).OR', OC(O).R', Aryl, C(O)OH
n=0.0 to 0.6 (mole ratio)
R is a hydrocarbyl group containing more than 10 carbon atoms, preferably from 10 to 30 carbon atoms R' is a $C_1$ to $C_{30}$ hydrocarbyl group.

Another monomer may be terpolymerized if necessary.

Examples of suitable comb polymers are the fumarate/vinyl acetate particularly those described in our European Patent Applications 0153176, 0153177, 85301047 and 85301048 and esterified olefine/maleic anhydride copolymers and the polymers and copolymers of alpha olefines and esterified copolymers of styrene and maleic anhydride.

Examples of other additives with which the compounds of the present invention may be used are the polyoxyalkylene esters, ethers, ester/ethers and mixtures thereof, particularly those containing at least one, preferably at least two $C_{10}$ to $C_{30}$ linear saturated alkyl groups and a polyoxyalkylene glycol group of molecular weight 100 to 5,000 preferably 200 to 5,000, the alkyl group in said polyoxyalkylene glycol containing from 1 to 4 carbon atoms. These materials form the subject of European Patent Publication 0,061,895 A2. Other such additives are described in U.S. Pat. No. 4,491,455.

The preferred esters, ethers or ester/ethers which may be used may be structurally depicted by the formula:

R—O(A)—O—R"

where R and R" are the same or different and may be i) n-alkyl ii) 
n-alkyl—C(=O)

iii) 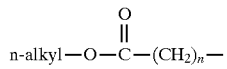
n-alkyl—O—C(=O)—(CH$_2$)$_n$— iv) 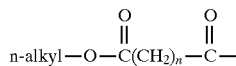
n-alkyl—O—C(=O)(CH$_2$)$_n$—C(=O)— the alkyl group being linear and saturated and containing 10 to 30 carbon atoms, and A represents the polyoxyalkylene segment of the glycol in which the alkylene group has 1 to 4 carbon atoms, such as polyoxymethylene, polyoxyethylene or polyoxytrimethylene moiety which is substantially linear; some degree of branching with lower alkyl side chains (such as in polyoxypropylene glycol) may be tolerated but it is preferred the glycol should be substantially linear, A may also contain nitrogen.

Suitable glycols generally are the substantially linear polyethylene glycols (PEG) and polypropylene glycols (PPG) having a molecular weight of about 100 to 5,000, preferably about 200 to 2,000. Esters are preferred and fatty acids containing from 10–30 carbon atoms are useful for reacting with the glycols to form the ester additives and it is preferred to use a $C_{18}$–$C_{24}$ fatty acid, especially behenic acids. The esters may also be prepared by esterifying polyethoxylated fatty acids or polyethoxylated alcohols.

Polyoxyalkylene diesters, diethers, ether/esters and mixtures thereof are suitable as additives with diesters preferred for use in narrow boiling distillates whilst minor amounts of monoethers and monoesters may also be present and are often formed in the manufacturing process.

It is important for additive performance that a major amount of the dialkyl compound is present. In particular, stearic or behenic diesters of polyethylene glycol, polypropylene glycol or polyethylene/polypropylene glycol mixtures are preferred.

The compounds of this invention may also be used with ethylene unsaturated ester copolymer flow improvers. The unsaturated monomers which may be copolymerised with ethylene include unsaturated mono and diesters of the general formula:

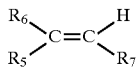

wherein $R_6$ is hydrogen or methyl, $R_5$ is a —OOCR$_8$ group wherein $R_8$ is hydrogen formate or a $C_1$ to $C_{28}$, more usually $C_1$ to $C_{17}$, and preferably a $C_1$ to $C_8$, straight or branched chain alkyl group; or $R_5$ is a —COOR$_8$ group wherein $R_8$ is as previously described but is not hydrogen and $R_7$ is hydrogen or —COOR$_8$ as previously defined. The monomer, when R6 and $R_7$ are hydrogen and R5 is —OOCR$_8$, includes vinyl alcohol esters of $C_1$ to $C_{29}$, more usually $C_1$ to C5, monocarboxylic acid, and preferably $C_2$ to $C_{29}$, more usually $C_1$ to C5 monocarboxylic acid, and preferably $C_2$ to $C_5$ monocarboxylic acid. Examples of vinyl esters which may be copolymerised with ethylene include vinyl acetate, vinyl propionate and vinyl butyrate or isobutyrate, vinyl acetate being preferred. We prefer that the copolymers contain from 5 to 40 wt. % of the vinyl ester, more preferably from 10 to 35 wt. % vinyl ester. They may also be mixtures of two copolymers such as those described in U.S. Pat. No. 3,961,916. It is preferred that these copolymers have a number average molecular weight as measured by vapour phase osmometry of 1,000 to 10,000, preferably 1,000 to 5,000.

The compounds of the invention may also be used in distillate fuels in combination with other polar compounds, either ionic or non-ionic, which have the capability in fuels of acting as wax crystal growth inhibitors. Polar nitrogen containing compounds have been found to be especially effective when used in combination with the glycol esters, ethers or ester/ethers and such three component mixtures are within the scope of the present invention. These polar compounds are generally amine salts and/or amides formed by reaction of at least one molar proportion of hydrocarbyl substituted amines with a molar proportion of hydrocarbyl acid having 1 to 4 carboxylic acid groups or their anhydrides; ester/amides may also be used containing 30 to 300, preferably 50 to 150 total carbon atoms. These nitrogen compounds are described in U.S. Pat. No. 4,211,534. Suitable amines are usually long chain $C_{12}$–$C_{40}$ primary, secondary, tertiary or quaternary amines or mixtures thereof but shorter chain amines may be used provided the resulting nitrogen compound is oil soluble and therefore normally containing about 30 to 300 total carbon atoms. The nitrogen compound preferably contains at least one straight chain $C_8$ to C40, preferably $C_{14}$ to $C_{24}$ alkyl segment.

Suitable amines include primary, secondary, tertiary or quaternary, but preferably are secondary. Tertiary and quaternary amines can only form amine salts. Examples of amines include tetradecyl amine, cocoamine, hydrogenated tallow amine and the like. Examples of secondary amines include dioctacedyl amine, methyl-behenyl amine and the like. Amine mixtures are also suitable and many amines derived from natural materials are mixtures. The preferred amine is a secondary hydrogenated tallow amine of the formula HNR$_1$R$_2$ where in $R_1$ and $R_2$ are alkyl groups derived from hydrogenated tallow fat composed of approximately 4% $C_{14}$, 31% $C_{16}$, 59% $C_{18}$.

Examples of suitable carboxylic acids and their anhydrides for preparing these nitrogen compounds include cyclohexane, 1,2 dicarboxylic acid, cyclohexene, 1,2-dicarboxylic acid, cyclopentane 1,2-dicarboxylic acid, naphthalene dicarboxylic acid and the like. Generally, these acids will have about 5–13 cabon atoms in the cyclic moiety. Preferred acids useful in the present invention are benzene dicarboxylic acids such as phthalic acid, isophthalic acid, and terephthalic acid. Phthalic acid or its anhydride is particularly preferred. The particularly preferred compound is the amide-amine salt formed by reacting 1 molar portion of phthalic anhydride with 2 molar portions of di-hydrogenated tallow amine. Another preferred compound is the diamide formed by dehydrating this amide-amine salt.

Hydrocarbon polymers may also be used as part of the additive combination which may be represented with the following general formula:

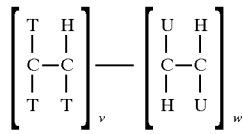

where

T=H or R'

U=H, T or Aryl v=1.0 to 0.0 (mole ratio)

w=0.0 to 1.0 (mole ratio)

where $R^1$ is alkyl.

These polymers may be made directly from ethylenically unsaturated monomers or indirectly by hydrogenating the polymer made from monomers such as isoprene, butadiene etc.

A particularly preferred hydrocarbon polymer is a copolymer of ethylene and propylene having an ethylene content preferably between 20 and 60% (w/w) and is commonly made via homogeneous catalysis.

The ratios of additives to be used will depend on the fuel to be treated but generally from 30 to 60 wt. % of the additives is the compounds of the invention.

The additive systems which form part of the present invention may conveniently be supplied as concentrates for incorporation into the bulk distillate fuel. These concentrates may also contain other additives as required. These concentrates preferably contain from 3 to 75 wt. %, more preferably 3 to 60 wt. %, most preferably 10 to 50 wt. % of the additives, preferably in solution in oil. Such concentrates are also within the scope of the present invention. The additives of this invention may be used in the broad range of distillate fuels boiling in the range 120° to 500° C.

The invention is illustrated by the following Examples.

PREPARATION

EXAMPLE 1

The N,N-dialkyl ammonium salt of 2-dialkylamido benzene sulphonate where the alkyl groups are $nC_{16}$-$_{18}$ $H_{33-37}$ was prepared by reacting 1 mole of ortho-sulphobenzoic acid cyclic anhydride with 2 moles of di-(hydrogenated) tallow amine in a xylene solvent at 50% (w/w) concentration. The reaction mixture was stirred at between 100° C. and the refluxing temperature. The solvent and chemicals should be kept as dry as possible so as not to enable hydrolysis of the anhydride.

The product was analysed by 500 MHz Nuclear Magnetic Resonance Spectroscopy and the spectrum which is attached hereto as FIG. 12 confirmed the structure to be

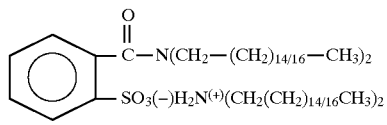

The molecular model of this compound is shown in FIG. 11.

EXAMPLE 2

Example 1 was repeated except that the ortho-sulphobenzoic acid was reacted first with 1 mole of octadecan-1-ol and 1 mole of di-hydrogenated tallow amine. The product was analysed by 500 MHz N.M.R. and the systems is attached hereto as FIG. 13 showing the structure to be

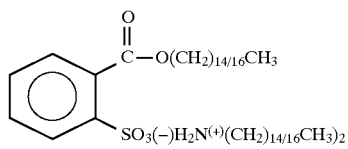

TESTING

The effectiveness of the product of Example 1 and additive systems containing the product as filterability improvers in distillate fuels were determined by the following methods.

By one method, the response of the oil to the additives was measured by the Cold Filter Plugging Point Test (CFPP) which is carried out by the procedure described in detail in "Journal of the Institute of Petroleum", Volume 52, Number 510, June 1966, pp. 173–285. This test is designed to correlate with the cold flow of a middle distillate in automotive diesels.

In brief, a 40 ml. sample of the oil to be tested is cooled in a bath which is maintained at about −34° C. to give non-linear cooling at about 1° C./min. Periodically (at each one degree C starting from above the cloud point), the cooled oil is tested for its ability to flow through a fine screen in a prescribed time period using a test device which is a pipette to whose lower end is attached an inverted funnel which is positioned below the surface of the oil to be tested. Stretched across the mouth of the funnel is a 350 mesh screen having an area defined by a 12 millimetre diameter. The periodic tests are each initiated by applying a vacuum to the upper end of the pipette whereby oil is drawn through the screen up into the pipette to a mark indicating 20 ml. of oil.

After each successful passage, the oil is returned immediately to the CFPP tube. The test is repeated with each one degree drop in temperature until the oil fails to fill the pipette within 60 seconds. This temperature is reported as the CFPP temperature. The difference between the CFPP of an additive free fuel and of the same fuel containing additive is reported as the CFPP depression by the additive. A more effective flow improver gives a greater CFPP depression at the same concentration of additive.

Another determination of flow improver effectiveness is made under conditions of the flow improver Programmed Cooling Test (PCT) which is a slow cooling test designed to idicate whether the wax in the fuel will pass through filters such as are found in heating oil distribution system.

In the test, the cold flow properties of the described fuels containing the additives were determined as follows. 300 ml.

of fuel are cooled linearly at 1° C./hour to the test temperature and the temperature then held constant. After 2 hours at −9° C., approximately 20 ml. of the surface layer is removed as the abnormally large wax crystals which tend to form on the oil/air interface during cooling. Wax which has settled in the bottle is dispersed by gentle stirring, then a CFPP filter assembly is inserted. The tap is opened to apply a vacuum of 500 mm. of mercury and closed when 200 ml. of fuel have passed through the filter into the graduated receiver. A PASS is recorded if the 200 ml. are collected within ten seconds through a given mesh size of a FAIL if the flow rate is too slow indicating that the filter has become blocked. CFPP filter assemblies with filter screens of 20, 30, 40, 60, 80, 100, 120, 150, 200, 250 and 350 mesh number are used to determine the finest mesh (largest mesh number) the fuel will pass. The larger the mesh number that a wax containing fuel will pass, the smaller are the wax crystals and the greater the effectiveness of the additive flow improver. It should be noted that no two fuels will give exactly the same test results at the same treatment level for the same flow improver additive.

Wax settling studies were also performed prior to PCT filtration. The extent of the setled layer was visually measured as a % of the total fuel volume. This extensive wax settling would be given by a low number whilst an unsettled fluid fuel would be at a state of 100%. Care must be taken because poor samples of gelled fuel with large wax crystals almost always exhibit high values, therefore these results should be recorded as "gel".

The effectiveness of the additives of the present invention in lowering the Cloud Point of distillate fuels was determined by the standard Cloud Point Test (IP-219 or ASTM-D 2500) other measures of the onset of crystallisation are the Wax Appearance Point (WAP) Test (ASTM D.3117-72) and the Wax Appearance Temperature (WAT) as measured by different scanning calorimetry using a Mettler TA 2000B differential scanning calorimeter. In the test a 25 microlitre sample of the fuel is cooled at 2° C./min. from a temperature at least 30° C. above the expected cloud point of the fuel. The observed onset of crystallisation is estimated, without correction for thermal lag (approximately 2° C.), as the wax appearance temperature as indicated by the differential scanning calorimeter.

The ability of the fuel to pass through a diesel vehicle main filter was determined in an apparatus consisting of a typical diesel vehicle main filter mounted in a standard housing in a fuel line; the Bosch Type as used in a 1980 VW Golf diesel passanger car, and a Cummins FF105 as used in the Cummins NTC engine series are appropriate. A reservoir and feed system capable of supplying half a normal fuel tank of fuel linked to a fuel injection pump as used in the VW Golf is used to draw fuel through the filter from the tank at constant flowrate, as in the vehicle. Instruments are provided to measure pressure drop across the filter, the flow rate from the injection pump and the unit temperatures. Receptables are provided to receive the pumped fuel, both "injected" fuel and the surplus fuel.

In the test the tank is filled with 19 Kilogrammes of fuel and leak tested. When satisfactory, the temperature is stabilised at an air temperature 8° C. above fuel cloud point. The unit is then cooled at 3° C./hour to the desired test temperature, and held for at least 3 hours for fuel temperature to stabilise. The tank is vigorously shaken to fully disperse the wax present; a sample is taken from the tank and 1 litre of fuel removed through a sample point on the discharge line immediately after the tank and returned to the tank. The pump is then started, with pump rpm set to equate to pump rpm at a 110 kph road speed. In the case of the VW Golf this is 1900 rpm, corresponding to an engine speed of 3800 rpm. Pressure drop across the filter and flow rate of fuel from the injection pump are monitored until fuel is exhausted, typically 30 to 35 minutes.

Providing fuel feed to the injectors can be held at 2 ml/sec (surplus fuel will be about 6.5–7 ml/sec) the result is a "PASS". A drop in feed fuel flow to the injectors signifies a "BORDERLINE" result; zero flow a "FAIL".

Typically, a "PASS" result may be associated with an increasing pressure drop across the filter, which may rise as high as 60 kPA. Generally considerable proportions of wax must pass the filter for such a result to be achieved. A "GOOD PASS" is characterised by a run where the pressure drop across the filter does not rise above 10 kPa, and is the first indication that most of the wax has passed through the filter, an excellent result has a pressure drop below 5 kPa.

Additionally, fuel samples are taken from "surplus" fuel and "injector feed" fuel, ideally every four minutes throughout the test. These samples, together with the pre-test tank samples, are compared by DSC to establish the proportion of feed wax that has passed through the filter. Samples of the pre-test fuel are also taken and SEM samples prepared from them after the test to compare wax crystal size and type with actual performance.

The following additives were used
(i) The Product of Example 1
(ii) Additives A

A1 is a 1:3 (w/w) mixture of two ethylene-vinyl acetate copolymers; A3 consisting of ethylene and about 38 wt. % vinyl acetate, and has a number average molecular weight of about 1800 (VPO) and A2 consisting of ethylene and about 17 wt. % vinyl acetate and has a number average molecular weight of about 3000 (VPO). A4 is a 50/50% mixture of A2 and A3.

A5 consists of a polymer containing 13.5 wt. % vinyl acetate and has a number average molecular weight of 3500 (VPO).

(iii) Additive B

Polyethylene glycol (PEG) esters and polypropylene glycol (PPG) esters were prepared by mixing one molar proportion of the polyethylene or polypropylene glycol with one or two molar proportions of the carboxylic acids for the "mono-" and "di-" esters respectively. Para-toluene sulphonic acid was added at 0.5 wt. % of the reactant mass as catalyst. The mixture was heated to 150° C. with stirring and a slow stream of nitrogen to distil off water of reaction. When the reaction was completed, as judged by the infrared spectrum, the product was poured out while molten and allowed to cool, giving a waxy solid.

PEG's and PPG's are usually referred to in combination with their molecular weights, e.g. PEG 600 is a 600 average molecular weight polyethylene glycol. This nomenclature has been continued here so PEG 600 dibehenate is the ester product of the reaction of two molar proportions of behenic acid with one mole of PEG 600 which is Additive B used herein.

(iv) Additive C

The reaction product of one mole of phthalic anhydride with two moles of dihydrogenated tallow amine, to form a half amide/half amine salt.

(v) Additive D

A copolymer of ethylene and propylene containing 56 wt. % ethylene and of number average molecular weight of 60,000.

(vi) Additives E $E_1$ was made by esterifying a 1:1 molar styrene-maleic anhydride copolymer with 2 moles of a 1:1 molar mixture of $C_{12}H_{25}OH$ and $C_{14}H_{29}OH$ per mole of anhydride groups were used in the esterification (slight excess, approximately 5% alcohol used) step using p-toluene sulphonic acid as the catalyst (1/10 mole) in xylene solvent. which gave a molecular weight (Mn) of 50,000 and contained 3% (w/w) untreated alochol.

Polymer E2 was created by using 2 moles of the $C_{14}H_{29}OH$ to esterify the styrene maleic anhydride copolymer and this too gave a number average molecular weight of 50,000 and contained 3.3% (w/w) free alcohol.

In these further Examples fuels were treated with the additives, then cooled to 10° C. below their Wax Appearance Temperature (WAT), and the wax crystal size measured from an electron scanning micrograph and the ability of the fuel to pass through a Cummins FT105 fuel filter was determined.

EXAMPLE 3

Characteristics of Fuel used

| | |
|---|---|
| Cloud point | −14° C. |
| Untreated CFPP | −16° C. |
| Wax Appearance Temperature | −18.6° C. |
| Initial Boiling Point | 178° C. |
| 20% | 230° C. |
| 90% | 318° C. |
| Final Boiling Point | 355° C. |
| Wax content at −25° C. | 1.1 wt. % |

An additive combination comprising 250 p.p.m. of each of the Product of Example 1, Additives A5 and $E_1$ were included in the fuels and tested at −25° C. and the wax crystal size was found to be 1200 nanometres long and above 90 wt. % of the wax passed through the Cummins FF105 filter.

During the test, passage of wax was further evidenced by observing the pressure drop over the filter, which only increased by 2.2 kPa.

EXAMPLE 4

Example 3 was repeated and the wax crystal size was found to be 1300 nanometres and the maximum pressure drop across the filter was 3.4 Kpa.

EXAMPLE 5

Characteristics of Fuel Used

| | |
|---|---|
| Cloud Point | 0° C. |
| Untreated CFPP | −5° C. |
| Wax Appearance Temperature | −2.5° C. |
| Initial Boiling Point | 182° C. |
| 20% | 220° C. |
| 90% | 354° C. |
| Final Boiling Point | 385° C. |
| Wax content at test temperature | 1.6 wt %. |

An additive combination of 250 p.p.m. of each of the Product of Example 1 and Additives A5 and $E_2$ were incorporated in the fuel and the wax crystal size was found to be 1500 nanometres and about 75 wt % of the wax passed through the Bosch 145434106 filter at the test temperature of −8.5° C. The maximum pressure drop across the filter was 6.5 Kpa.

EXAMPLE 6

Example 5 was repeated and found to give wax crystal size 2000 nanometres long of which about 50 wt. % passed through filter giving a maximum pressure drop of 35.3 Kpa.

EXAMPLE 7

The fuel used in Example 5 was treated with 400 ppm of the product of Example 1 and 100 ppm of A1, the fuel was tested as in Example 5 at −8° C. at which temperature the wax content 1.4 wt. %. The wax crystal size was found to be 2500 nanometres and 50 wt. % of the wax passed through the filter with a pressure drop of 67.1 Kpa.

When using this fuel in the test rig, pressure drop rose rather quickly and the test failed. We believe this is because as shown in the photograph the crystals are flat and flat crystals that fail to pass the filter tend to cover the filter with a thin, impermeable layer. "Cube like" (or "nodular") crystals on the other hand when not passing through the filters, collect in a comparatively loose "cake", through which fuel can still pass until the mass becomes so great that the filter fills and the total thickness of wax "cake" is so great that the pressure drop again is excessive.

EXAMPLE 8 (COMPARATIVE)

The fuel used in Example 5 was treated with 500 ppm of a mixture of 4 parts of Additive C and 1 part of Additive A5 and tested at −8° C., the wax crystal size was found to be 6300 nanometres and 13 wt. % of the wax passed through the filter.

This example is among the very best examples of the prior art, but without crystal passage.

These were prepared by placing samples of fuel in 2 oz. bottles in cold boxes held about 8° C. above fuel cloud point for 1 hour while fuel temperature stabilises. The box is then cooled at 1° C. an hour down to the test temperature, which is then held.

A pre-prepared filter carrier, consisting of a 10 mm diameter sintered ring, surrounded with a 1 mm wide annular metal ring, supporting a 200 nanometres rated silver membrane filter which is held in position by two vertical pins, is then placed on a vacuum unit. A vacuum of at least 30 kPa is applied, and the cooled fuel dripped onto the membrane from a clean dropping pipette until a small domed puddle just covers the membrane. The fuel is dropped slowly to sustain the puddle; after about 10–20 drops of fuel have been applied the puddle is allowed to drain down leaving a thin dull matt layer of fuel wet wax cake on the membrane. A thick layer of wax will not wash acceptably, and a thin one may be washed away. The optimal layer thickness is a function of crystal shape, with "leafy" crystals needing thinner layers than "nodular" crystals. It is important that the final cake have a matt appearance. A "shiny" cake indicates excessive residual fuel and crystal "smearing" and should be discarded.

The cake is then washed with a few drops of methyl ethyl ketone which are allowed to completely drain away. The process is repeated a number of times. When washing is complete the methyl ethyl ketone will disappear very quickly, leaving a "brilliant matt white" surface which will turn grey on application of another drop of methyl ethyl ketone.

The washed sample is then placed in a cold dessicator, and kept until ready for coating in the SEM. It may be necessary to keep the sample refrigerated to preserve the wax, in which case it should be stored in a cold box prior to transfer (in a suitable sample transfer container) to the SEM to avoid ice crystal formation on the sample surface.

During coating, the sample must be kept as cold as possible to minimise damage to the crystals. Electrical contact with the stage is best provided for by a retaining screw pressing the annular ring against the side of a well in the stage designed to permit the sample surface to lie on the instrument focal plane. Electrically conductive paint can also be used.

Once coated, the micrographs are obtained in a conventional way on the Scanning Electron Microscope. The photomicrographs are analysed to determine the average crystal size by fastening a transparent sheet with 88 points marked (as dots) at the intersections of a regular, evenly spaced grid 8 rows and 11 columns in size, to a suitable micrograph. The magnification should be such that only a few of the largest crystal are touched by more than one dot and 4000 to 8000 times have proved suitable. At each grid point, if the dot touches a crystal dimension whose shape can be clearly defined, the crystal may be measured. A measure of "scatter", in the form of the Gaussian standard deviation of crystal length with Bessel correction applied is also taken.

Examples 3 to 7, therefore show that when using the compounds of the invention in additive formulations crystals can pass through the filter reliably and the excellent cold temperature performance can be extended to higher fuel wax contents than heretofore practicable and also at temperatures further below fuel Wax Appearance Temperature than heretofore practicable without regard to fuel system considerations such as the ability of recycle fuel from the engine to warm the feed fuel being drawn from the fuel tank, the ratio of feed fuel flow to recycle fuel, the ratio of main filter surface area to feed fuel flow and the size and position of prefilters and screens.

The compound produced in Example 1 was tested for its effectiveness as an additive for distillate fuel in the following Fuels, the boiling characteristic being measured by the ASTM-D86 test.

The results in the Programme Cooling Test carried out at −12° C. in Fuel 1 were as follows.

| Additive Used and their proportions | | | | | Smallest Mesh Passed at | | | Settling | | |
|---|---|---|---|---|---|---|---|---|---|---|
| C | Example 1 | A2 | B | A3 | 50* | 100* | 200* | Wax Level % | | |
| 1 | — | — | — | — | 30 | 40 | 80 | 20 | 5 | 2 |
| 4 | — | 1 | — | — | 80 | 100 | 200 | 10 | 5 | 5 |
| 4 | — | — | 1 | — | 40 | 80 | 200 | 15 | 10 | 5 |
| — | 1 | — | — | — | 60 | 120 | 250 | 10 | 100 | 100 |
| — | 4 | 1 | — | — | 150 | 350 | 350 | 50 | 100 | 100 |
| — | 4 | — | 1 | — | 120 | 200 | 250 | 10 | 50 | 100 |
| — | — | 1 | — | — | — | 40 | 60 | — | 10 | 10 |
| — | — | — | — | 1 | — | 60 | 120 | — | 20 | 40 |
| — | — | 1 | — | 3 | — | 60 | 120 | — | 20 | 40 |
| — | — | — | 1 | 4 | — | 80 | 150 | — | 15 | 15 |
| None | | | | | 30 | | | gel | | |

*total ppm concentration of additive.

Further results in Fuel 1 were as follows:

| | | Finest PCT Mesh passed at −11° C. | |
|---|---|---|---|
| Additive | | 150 | 250 ppm ai |
| A1 | | 100 | 200 |
| C | | 60 | 120 |
| Example 1 | | 200 | 350 |
| Example 2 | | 150 | 250 |
| C/A2 | (4/1) | 100 | 350 |
| Example 1/A2 | (4/1) | 350 | 350 |
| Example 2/A2 | (4/1) | 200 | 350 |
| C | (9/1) | 150 | 250 |
| Example 1/B | (9/1) | 250 | 350 |
| C/D | (9/1) | 150 | 350 |
| Example 1/D | (9/1) | 350 | 350 |
| None | | 30 | |

Results in Fuel 3 were as follows:

| | | Finest PCT mesh passed at −5° C. | | |
|---|---|---|---|---|
| Additive | | 400 ppm | 600 ppm | Wax Level (%) |
| A1 | | 40 | 60 | 10 |
| C | | 40 | 100 | 10 |
| Example 1 | | 80 | 200 | 100 |
| D/C | (1/4) | 40 | 120 | 10 |
| D/Example 1 | (1/4) | 80 | 250 | 100 |
| None | | 20 | | gel |

| | | | Distillation ASTM-D86 | | | | | |
|---|---|---|---|---|---|---|---|---|
| | Cloud Point | Wax Appearance Point | Initial Boiling Point | 20 | 50 | 90 | Final Boiling Point | Untreated CFPP |
| Fuel 1 | −3.0 | −5.0 | 180 | 223 | | 336 | 365 | ±5.0 |
| Fuel 2 | +3.0 | +1.0 | 188 | 236 | 278 | 348 | 376 | 0 |
| Fuel 3 | +5.0 | 0.0 | 228 | 280 | 310 | 351 | 374 | −1 |

Further results in Fuel 1 are as follows:

| Additive 1 | Additive 2 | Ratio | Treat Rate | Wax Settling State* % | PCT* at | CFPP (°C.) |
|---|---|---|---|---|---|---|
| A2 | | | 100 | 10 | 60 | −11.0 |
| A2 | | | 200 | | 60 | −14.0 |
| A2 | | | 300 | 40 | | −13.5 |
| A2 | C | 4.1 | 100 | | 30 | −12.0 |
| A2 | C | 4.1 | 200 | 30 | 30 | −11.0 |
| A2 | C | 4.1 | 300 | 20 | 40 | −14.0 |
| A2 | C | 1.1 | 100 | 10 | 60 | −13.5 |
| A2 | C | 1.1 | 200 | 10 | 80 | |
| A2 | C | 1.1 | 300 | 15 | 200 | −18.0 |
| A2 | C | 1.4 | 100 | 10 | 80 | 9.0 |
| A2 | C | 1.4 | 200 | 5 | 100 | −18.5 |
| A2 | C | 1.4 | 300 | 20 | 350 | −18.5 |
| A2 | Ex. 1 | 4.1 | 100 | 20 | 40 | −13.0 |
| A2 | Ex. 1 | 4.1 | 200 | 20 | 40 | −14.5 |
| A2 | Ex. 1 | 4.1 | 300 | 25 | 40 | −15.0 |
| A2 | Ex. 1 | 1.1 | 100 | 100 | 150 | −17.0 |
| A2 | Ex. 1 | 1.1 | 200 | 100 | 350 | −18.0 |
| A2 | Ex. 1 | 1.1 | 300 | 100 | 350 | −19.5 |
| A2 | Ex. 1 | 1.4 | 100 | 100 | 350 | −17.0 |
| A2 | Ex. 1 | 1.4 | 200 | 100 | 350 | −19.5 |
| A2 | Ex. 1 | 1.4 | 300 | 100 | 350 | −19.5 |
| None | None | — | — | gel | 30 | −5.0 |
| A4 | | | 100 | 20 | 60 | −14.0 |
| A4 | | | 200 | 25 | 80 | −16.0 |
| A4 | | | 300 | 30 | 120 | −16.5 |
| A4 | C | 4.1 | 100 | 15 | 60 | −15.0 |
| A4 | C | 4.1 | 200 | 20 | 100 | −16.5 |
| A4 | C | 4.1 | 300 | 20 | 200 | −17.0 |
| A4 | C | 1.1 | 100 | 10 | 80 | −11.0 |
| A4 | C | 1.1 | 200 | 15 | 250 | −17.5 |
| A4 | C | 1.1 | 300 | 15 | 250 | −20.0 |
| A4 | C | 1.4 | 100 | 5 | 100 | −6.5 |
| A4 | C | 1.4 | 200 | 10 | 200 | −16.5 |
| A4 | C | 1.4 | 300 | 10 | 120 | −19.0 |
| A4 | Ex. 1 | 4.1 | 100 | 10 | 89 | −13.0 |
| A4 | Ex. 1 | 4.1 | 200 | 15 | 100 | −16.5 |
| A4 | Ex. 1 | 4.1 | 300 | 20 | 250 | −18.0 |
| A4 | Ex. 1 | 1.1 | 100 | 10 | 80 | −17.5 |
| A4 | Ex. 1 | 1.1 | 200 | 15 | 80 | −16.0 |
| A4 | Ex. 1 | 1.1 | 300 | 100 | 150 | −25.5 |
| A4 | Ex. 1 | 1.4 | 100 | 100 | 250 | −19.0 |
| A4 | Ex. 1 | 1.4 | 200 | 100 | 350 | −21.0 |
| A4 | Ex. 1 | 1.4 | 300 | 100 | 350 | −22.5 |
| None | None | — | — | gel | 30 | −5.0 |
| A1 | | | 100 | 20 | 80 | −16.0 |
| A1 | | | 200 | 40 | 120 | −17.0 |
| A1 | | | 300 | 40 | 200 | −17.5 |
| A1 | C | 4.1 | 100 | 15 | 100 | −15.0 |
| A1 | C | 4.1 | 200 | 30 | 200 | −19.0 |
| A1 | C | 4.1 | 300 | 40 | 250 | −19.5 |
| A1 | C | 1.1 | 100 | 10 | 150 | −14.5 |
| A1 | C | 1.1 | 200 | 30 | 200 | −19.5 |
| A1 | C | 1.1 | 300 | 25 | 250 | −22.0 |
| A1 | C | 1.4 | 100 | 20 | 150 | −15.0 |
| A1 | C | 1.4 | 200 | 100 | 150 | −19.0 |
| A1 | C | 1.4 | 300 | 100 | 350 | −20.0 |
| A1 | Ex. 1 | 4.1 | 100 | 20 | 120 | −14.5 |
| A1 | Ex. 1 | 4.1 | 200 | 100 | 150 | −19.5 |
| A1 | Ex. 1 | 4.1 | 300 | 100 | 200 | −24.5 |
| A1 | Ex. 1 | 1.1 | 100 | 10 | 150 | −18.0 |
| A1 | Ex. 1 | 1.1 | 200 | 25 | 200 | −24.5 |
| A1 | Ex. 1 | 1.1 | 300 | 25 | 250 | −25.0 |
| A1 | Ex. 1 | 1.4 | 100 | 100 | 150 | −18.5 |
| A1 | Ex. 1 | 1.4 | 200 | 100 | 350 | −20.5 |
| A1 | Ex. 1 | 1.4 | 300 | 100 | 350 | −24.5 |
| None | None | — | — | gel | 30 | −5.0 |
| A3 | | | 100 | 20 | 80 | −9.5 |
| A3 | | | 200 | 40 | 150 | −14.0 |
| A3 | | | 300 | 70 | 200 | −19.0 |
| A3 | C | 4.1 | 100 | 10 | 100 | −6.5 |
| A3 | C | 4.1 | 200 | 20 | 200 | −11.0 |
| A3 | C | 4.1 | 300 | 25 | 250 | −16.0 |
| A3 | C | 1.1 | 100 | 5 | 80 | −5.0 |
| A3 | C | 1.1 | 200 | 15 | 200 | −6.5 |
| A3 | C | 1.1 | 300 | 30 | 250 | −7.5 |
| A3 | C | 1.4 | 100 | 10 | 40 | −4.5 |
| A3 | C | 1.4 | 200 | 10 | 120 | −4.5 |
| A3 | C | 1.4 | 300 | 15 | 150 | −5.5 |
| A3 | Ex. 1 | 4.1 | 100 | 10 | 100 | −6.0 |
| A3 | Ex. 1 | 4.1 | 200 | 20 | 150 | −9.5 |
| A3 | Ex. 1 | 4.1 | 300 | 25 | 200 | −16.0 |
| A3 | Ex. 1 | 1.1 | 100 | 5 | 80 | −5.5 |
| A3 | Ex. 1 | 1.1 | 200 | 20 | 150 | −8.0 |
| A3 | Ex. 1 | 1.1 | 300 | 20 | 120 | −16.5 |
| A3 | Ex. 1 | 1.4 | 100 | 5 | 40 | −4.0 |
| A3 | Ex. 1 | 1.4 | 200 | 10 | 60 | −6.5 |
| A3 | Ex. 1 | 1.4 | 300 | 25 | 150 | −9.0 |
| None | None | — | — | gel | 30 | −5.0 |

*at −12° C.

Results in Fuel 2 were as follows

| Additive 1 | Additive 2 | Ratio | Treat Rate | Wax Settling State* % | PCT* at | CFPP (°C.) |
|---|---|---|---|---|---|---|
| A2 | | | 300 | 25 | 30 | −4.5 |
| A2 | | | 500 | 20 | 40 | −9.5 |
| A2 | | | 700 | 15 | 60 | −11.0 |
| A2 | C | 4.1 | 300 | 15 | 60 | −11.0 |
| A2 | C | 4.1 | 500 | 15 | 60 | −12.0 |
| A2 | C | 4.1 | 700 | 15 | 40 | −15.0 |
| A2 | C | 1.1 | 300 | 20 | 40 | −15.0 |
| A2 | C | 1.1 | 500 | 10 | 80 | −16.0 |
| A2 | C | 1.1 | 700 | 20 | 200 | −15.5 |
| A2 | C | 1.4 | 300 | 10 | 100 | −12.5 |
| A2 | C | 1.4 | 500 | 10 | 200 | −14.0 |
| A2 | C | 1.4 | 700 | 100 | 250 | −15.0 |
| A2 | Ex. 1 | 4.1 | 300 | 15 | 40 | −7.5 |
| A2 | Ex. 1 | 4.1 | 500 | 15 | 60 | −17.0 |
| A2 | Ex. 1 | 4.1 | 700 | 20 | 100 | −19.0 |
| A2 | Ex. 1 | 1.1 | 300 | 10 | 80 | −14.5 |
| A2 | Ex. 1 | 1.1 | 500 | 15 | 120 | −18.0 |
| A2 | Ex. 1 | 1.1 | 700 | 20 | 150 | −18.0 |
| A2 | Ex. 1 | 1.4 | 300 | 100 | 150 | −18.0 |
| A2 | Ex. 1 | 1.4 | 500 | 100 | 350 | −15.0 |
| A2 | Ex. 1 | 1.4 | 700 | 100 | 350 | −20.0 |
| None | None | — | — | gel | 30 | 0.0 |
| A4 | | | 300 | 30 | 100 | −15.5 |
| A4 | | | 500 | 35 | 120 | −15.5 |
| A4 | | | 700 | 45 | 120 | −16.5 |
| A4 | C | 4.1 | 300 | 20 | 100 | −15.0 |
| A4 | C | 4.1 | 500 | 20 | 120 | −15.0 |
| A4 | C | 4.1 | 700 | 25 | 150 | −15.0 |
| A4 | C | 1.1 | 300 | 10 | 100 | −15.0 |
| A4 | C | 1.1 | 500 | 25 | 150 | −17.5 |
| A4 | C | 1.1 | 700 | 20 | 200 | −18.5 |
| A4 | C | 1.4 | 300 | 10 | 120 | −11.5 |
| A4 | C | 1.4 | 500 | 15 | 200 | −15,5 |
| A4 | C | 1.4 | 700 | 20 | 250 | −14.5 |
| A4 | Ex. 1 | 4.1 | 300 | 15 | 100 | −17.0 |
| A4 | Ex. 1 | 4.1 | 500 | 25 | 120 | −17.0 |
| A4 | Ex. 1 | 4.1 | 700 | 25 | 150 | −19.5 |
| A4 | Ex. 1 | 1.1 | 300 | 10 | 120 | −13.5 |
| A4 | Ex. 1 | 1.1 | 500 | 15 | 200 | −19.0 |
| A4 | Ex. 1 | 1.1 | 700 | 20 | 250 | −21.0 |
| A4 | Ex. 1 | 1.4 | 300 | 100 | 150 | |
| A4 | Ex. 1 | 1.4 | 500 | 100 | 350 | |
| A4 | Ex. 1 | 1.4 | 700 | 100 | 350 | −18.5 |
| None | None | — | — | gel | 30 | 0.0 |
| A1 | | | 300 | 40 | 120 | −15.0 |

-continued

| Additive | | Treat Ratio | Rate | Wax Settling State* % | PCT* at | CFPP (°C.) |
|---|---|---|---|---|---|---|
| 1 | 2 | | | | | |
| A1 | | | 500 | 40 | 150 | −19.0 |
| A1 | | | 700 | 60 | 200 | −18.5 |
| A1 | C | 4.1 | 300 | 25 | 120 | −15.0 |
| A1 | C | 4.1 | 500 | 30 | 150 | −14.0 |
| A1 | C | 4.1 | 790 | 50 | 200 | −17.0 |
| A1 | C | 1.1 | 300 | 15 | 120 | −17.0 |
| A1 | C | 1.1 | 500 | 25 | 150 | −16.0 |
| A1 | C | 1.1 | 700 | 25 | 200 | −19.0 |
| A1 | C | 1.4 | 300 | 15 | 80 | −13.0 |
| A1 | C | 1.4 | 500 | 15 | 120 | −13.0 |
| A1 | C | 1.4 | 700 | 15 | 250 | −15.0 |
| A1 | Ex. 1 | 4.1 | 300 | 20 | 120 | −18.0 |
| A1 | Ex. 1 | 4.1 | 500 | 30 | 200 | −16.5 |
| A1 | Ex. 1 | 4.1 | 700 | 40 | 250 | −15.0 |
| A1 | Ex. 1 | 1.1 | 300 | 15 | 120 | −15.5 |
| A1 | Ex. 1 | 1.1 | 500 | 25 | 250 | −20.0 |
| A1 | Ex. 1 | 1.1 | 700 | 25 | 350 | −19.5 |
| A1 | Ex. 1 | 1.4 | 300 | 100 | 150 | −16.5 |
| A1 | Ex. 1 | 1.4 | 500 | 100 | 350 | −20.0 |
| A1 | Ex. 1 | 1.4 | 700 | 100 | 350 | −19.0 |
| None | None | — | — | gel | 30 | 0.0 |
| A3 | | | 300 | 40 | 100 | −13.5 |
| A3 | | | 500 | 40 | 100 | |
| A3 | | | 700 | 40 | 150 | |
| A3 | C | 4.1 | 300 | 30 | 150 | −14.5 |
| A3 | C | 4.1 | 500 | 40 | 150 | −17.0 |
| A3 | C | 4.1 | 700 | 50 | 200 | −15.5 |
| A3 | C | 1.1 | 300 | 30 | 150 | −9.5 |
| A3 | C | 1.1 | 500 | 40 | 200 | −14.5 |
| A3 | C | 1.1 | 700 | 40 | 250 | −12.5 |
| A3 | C | 1.4 | 300 | 20 | 100 | −3.0 |
| A3 | C | 1.4 | 500 | 20 | 120 | −7.0 |
| A3 | C | 1.4 | 700 | 20 | 250 | −12.0 |
| A3 | Ex. 1 | 4.1 | 300 | 40 | 120 | −13.0 |
| A3 | Ex. 1 | 4.1 | 500 | 40 | 150 | −15.0 |
| A3 | Ex. 1 | 4.1 | 700 | 50 | 200 | −15.0 |
| A3 | Ex. 1 | 1.1 | 300 | 30 | 150 | −7.0 |
| A3 | Ex. 1 | 1.1 | 500 | 40 | 200 | −13.5 |
| A3 | Ex. 1 | 1.1 | 700 | 60 | 250 | −14.0 |
| A3 | Ex. 1 | 1.4 | 300 | 20 | 150 | −6.5 |
| A3 | Ex. 1 | 1.4 | 500 | 100 | 350 | −13.5 |
| A3 | Ex. 1 | 1.4 | 700 | 100 | 350 | −17.0 |
| None | None | — | — | gel | 30 | 0.0 |

*at −7° C.

EXAMPLE 9

The fuel used in this Example had the following characteristics:

| (ASTM-D86) | |
|---|---|
| IBP | 190° C. |
| 20% | 246° C. |
| 90% | 346° C. |
| FBP | 374° C. |
| Wax Appearance Temperature | −1.5° C. |
| Cloud Point | +2.0° C. |

It was treated with 1000 parts per million of active ingredient of the following additives:

(E) A mixture of Additive 2 (1 part by weight) and Additive 4 (9 parts by weight).

(F) The commercial ethylene vinyl acetate copolymer additive marketed by Exxon Chemicals as ECA 5920.

(G) A mixture of:
1 part Additive 1
1 part Additive 3
1 part Additive D
1 part of Additive K (H) The commercial ethylene vinyl acetate copolymer additive marketed by Amoco as 2042E.

(I) The commercial ethylene vinyl propionate copolymer additive marketed by BASF as Keroflux 5486.

(J) No additive.

(K) The reaction product of 4 moles of di-hydrogenated-tallow amine and 1 mole of pyromellitic anhydride. The reaction is performed solventless at 150° C., stirring under nitrogen for 6 hours.

The following performance characteristics of these fuels were then measured.

(i) The ability of the fuel to pass through the diesel fuel main filter at −9° C., and the percentage of wax passing through the filter with the following results:

| Additive | Time to Failure | % of Wax Passing |
|---|---|---|
| E | 11 minutes | 18–30% |
| F | 16 minutes | 30% |
| G | No Failure | 90–100% |
| H | 15 minutes | 25% |
| I | 12 minutes | 25% |
| J | 9 minutes | 10% |

Figure 14:
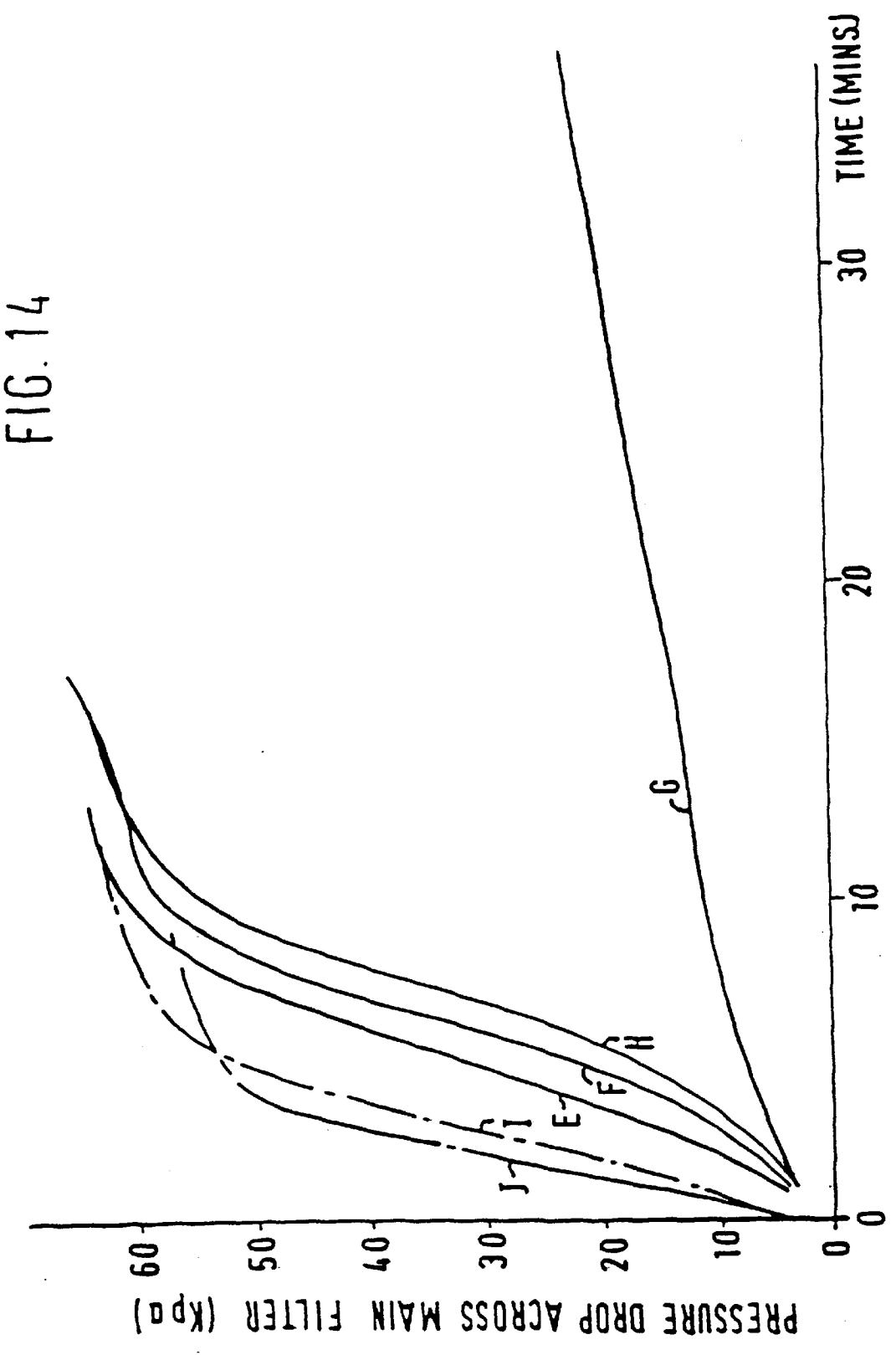
FIG. 14 is a graph depicting the pressure drop across a filter versus time for the wax in Example 9.

(ii) The pressure drop across the main filter against time is indicative of any wax passing through the filter and the results are shown graphically in FIG. 14.

(iii) The wax settling in the fuels was measured by cooling 100 mls of fuel in a graduated measuring cylinder. The cylinder is cooled at 1° C./hour from a temperature preferably 10° C. above the fuel's Cloud Point but not less than 5° C. above the fuel's Cloud Point to the test temperature, which is then held for a prescribed time. The test temperature and soak time depend upon the application, i.e. diesel fuel and heating oil. It is preferred that the test temperature be at least 5° C. below the Cloud Point and the minimum cold soak time at the test temperature be at least 4 hours. Preferably the test temperature should be 10° C. or more below the fuel's Cloud Point and the soak period should be 24 hours or more.

After the end of the soak period the measuring cylinder is examined and the extent of wax crystal settling is visually measured as the height of any wax layer above the bottom of the cylinder (0 mls) and expressed in terms of a percentage of the total volume (100 mls). Clear fuel may be seen above the settled wax crystals and this form of measurement is often sufficient to form a judgement on the wax settling. Sometimes the fuel is cloudy above a settled wax crystal layer or the wax crystals can be seen to be visibly denser as they approach the bottom of the cylinder. In this case a more quantitative method of analysis is used. Here the top 5% (5 mls) of fuel is sucked off carefully and stored, the next 45% is sucked off and discarded, the next 5% is sucked off and stored, the next 35% is sucked off and discarded and finally the bottom 10% is collected after warming to dissolve the wax crystals. These stored samples will henceforth be referred to as Top, Middle and Bottom samples respectively. It is important that the vacuum applied to remove the samples be fairly low, i.e. 200 mm water pressure, and that the top of the pipette is placed just on the surface of the fuel to avoid currents in the liquid which could disturb the concentration of wax at different layers within the cylinder. The samples are then warmed to 60° C. for 15 minutes and examined for wax content by Differential Scanning Calorimetry (DSC) as previously described.

In this instance a Mettler TA 2000B DSC. machine was used. A 25 ul sample is placed in the sample cell and regular kerosine in the reference cell then they are cooled at 2° C./minute from 60° C. to at least 10° C. but preferably 20° C. above the Wax Appearance Temperature (WAT) then it is cooled at 2° C./minute to approximately 20° C. below the WAT. A reference must be run of the unsettled, uncooled treated fuel. The extent of wax settling then correlates with the WAT (or $\Delta$WAT=WAT settled sample—WAT original). Negative values indicate dewaxing of the fuel and positive values indicate wax enrichment through settling. The wax content may also be used as a measure of settling from these samples. This is illustrated by % WAX or $\Delta$% WAX ($\Delta$% Wax=% Wax settled sample—% Wax original) and, once again negative values indicate dewaxing of the fuel and positive values indicate wax enrichment through settling.

In this example the fuel was cooled at 1° C./hr from +10° C. down to −9° C. and cold soaked for 48 hours prior to testing. The results were as follows:

| Additive | Visual Wax Settling | WAT °C. Data Settled Samples | | |
|---|---|---|---|---|
| | | Top 5% | Middle 5% | Bottom 10% |
| E | Cloudy throughout Denser at bottom | −10.86 | −4.00 | −3.15 |
| F | 50% clear above | −13.35 | −0.80 | −0.40 |
| G | 100% | −7.85 | −7.40 | −7.50 |
| H | 35% clear above | −13.05 | −8.50 | +0.50 |
| I | 65% clear above | | | |
| J | 100% semi-gel | −6.20 | −6.25 | −6.40 |

Figure 15:
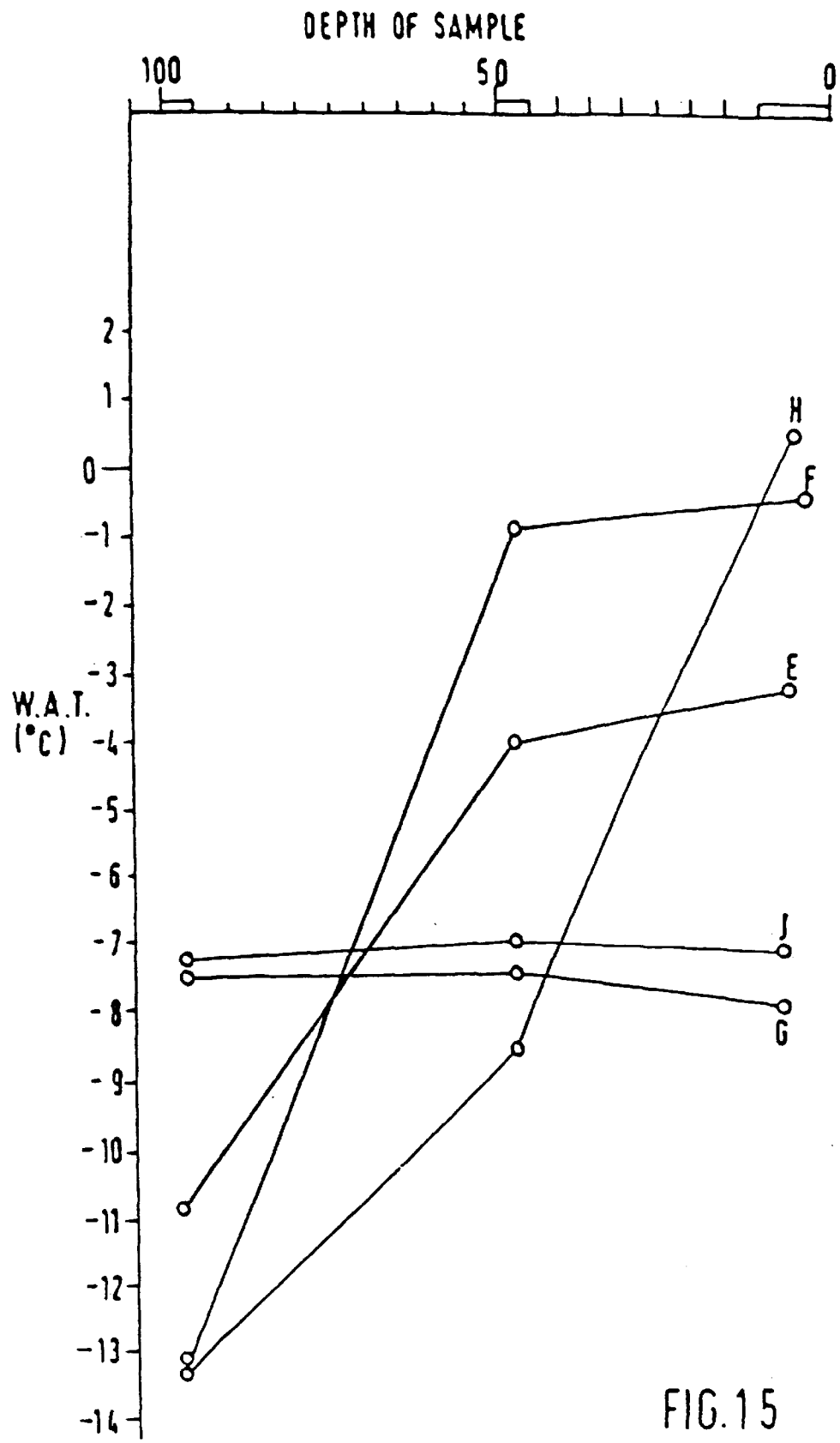
FIG. 15 is a graph depicting the depth of the sample versus temperature for the wax in Example 9.

(The results are also shown graphically in FIG. 15).

| | WAT original (Unsettled Fuel) | WAT(°C.) (Settled Samples) | | |
|---|---|---|---|---|
| | | Top 5% | Middle 5% | Bottom 10% |
| E | −6.00 | −4.80 | +2.00 | +2.85 |
| F | −5.15 | −8.20 | +4.35 | +4.75 |
| G | −7.75 | −0.10 | +0.35 | +0.25 |
| H | −5.00 | −8.05 | −3.50 | +4.50 |
| J | −6.20 | 0.00 | −0.05 | −0.20 |

(Note that significant depression of the WAT can be achieved by the most effective additive (G))

| | $\Delta$ % WAX (Settled Samples) | | |
|---|---|---|---|
| | Top 5% | Middle 5% | Bottom 10% |
| E | −0.7 | +0.8 | +0.9 |
| F | −0.8 | +2.1 | +2.2 |
| G | ±0.0 | +0.3 | +0.1 |
| H | −1.3 | −0.2 | +1.1 |
| J | −0.1 | ±0.0 | ±0.1 |

These results show that as the crystal size is reduced by the presence of additives, the wax crystals settle relatively quickly. For example, untreated fuels when cooled below their cloud points tend to show little wax crystal settling because the plate-like crystals interlock and cannot tumble freely in the liquid and a gel-like structure is set up but when a flow improver is added the crystals may be modified so their habit becomes less plate-like and tends to form needles of sizes in the range of tens of micrometers which can move freely in the liquid and settle relatively rapidly. This wax crystal settling can cause problems in storage tanks and vehicle systems. Concentrated wax layers may be unexpectedly drawn off, especially when the fuel level is low or the tank disturbed (e.g. when a vehicle corners), and filter blockage may occur.

If the wax crystal size can be reduced still further to below 10000 nanometres then the crystals settle relatively slowly and Wax Anti Settling can result giving the benefits in fuel performance compared to the case of a fuel with settled wax crystals. If the wax crystal size can be reduced to below approximately 4000 nanometres then the tendency of the crystals to settle is almost eliminated within the time of fuel storage. If the crystal sizes are reduced to the preferred size of below 2000 nanometres claim then the wax crystals remain suspended in the fuel for the many weeks required in some storage systems and the problems of settling are substantially eliminated.

(iv) The CFPP performance which was as follows:

| Additive | CFPP Temperature(°C.) | CFPP Depression |
|---|---|---|
| E | −14 | 11 |
| F | −20 | 17 |
| G | −20 | 17 |
| H | −20 | 17 |
| I | −19 | 16 |
| J | −3 | — |

(v) The average crystal size which was found to be:

| Additive | Size (Nanometers) |
|---|---|
| E | 4400 |
| F | 10400 |
| G | 2600 |
| H | 10000 |
| I | 8400 |
| J | Thin plates in excess of 50000 |

We claim:
1. At least one compound of the general formula

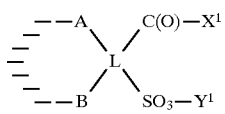

where
A and B may be the same or different and may be alkyl, alkenyl or aryl;
L is selected from the group consisting of
>CH—CH<
and >C=C<
and A, B and L together can constitute part of a cyclic structure which can be aromatic, alicyclic or mixed aromatic/alicyclic, and with the proviso that the groups —C(O)—$X^1$ and $SO_3$—$Y^1$ are located on different carbon atoms constituting L and in that when A, B and L do not constitute part of a cyclic structure one of A or B may be hydrogen and in that when L is non-cyclic ethylenic, said C(O)—$X^1$ and $SO_3$—$Y^1$ groupings are present in a cis configuration;
$X^1$ is —$NR^3R^1$;

$Y^1$ is selected from the group consisting of
$N^{(+)}R_3^3R^2$, $N^{(+)}HR_2^3R^2$, $N^{(+)}H_2R^3R^2$ and $N^{(+)}H_3R^2$;
and wherein $R^1$ and $R^2$ are straight chain or branched at the 1 or 2 position, and are independently selected from the group consisting of alkyl, alkoxy alkyl or polyalkoxyalkyl groups containing at least 10 carbon atoms in their main chain;
$R^3$ is hydrocarbyl and each $R^3$ is the same or different.

2. An aromatic substituted or unsubstituted compound of the general formula

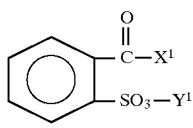

wherein $X^1$ is —$NR^3R^1$ and
$Y^1$ is $N^{(+)}R_3^3R^2$, $N^{(+)}H_2R^3R^2$ or $N^{(+)}H_3R^2$, and wherein $R^1$ and $R^2$ are straight chain or branched at the 1 or 2 position and are independently selected from the group consisting of alkyl, alkoxy alkyl, or polyoxyalkyl groups containing at least 10 carbon atoms in their main chain and $R^3$ is hydrocarbyl and each $R^3$ is the same or different.

3. An aromatic substituted or unsubstituted compound of the general formula

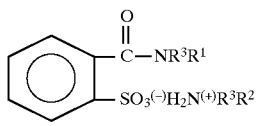

wherein $R^1$ and $R^2$ are straight chain or branched at the 1 or 2 position and are independently selected from the group consisting of alkyl, alkoxy alkyl, or polyoxyalkyl groups containing at least 10 carbon atoms in their main chain and $R^3$ is hydrocarbyl and each $R^3$ is the same or different.

4. An aromatic substituted or unsubstituted compound of the general formula

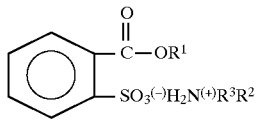

wherein $R^1$ and $R^2$ are straight chain or branched at the 1 or 2 position and are independently selected from the group consisting of alkyl, alkoxy alkyl, or polyoxyalkyl groups containing at least 10 carbon atoms in their main chain and $R^3$ is hydrocarbyl and each $R^3$ is the same or different.

5. Distillate fuel boiling in the range 120° C. to 500° C. containing 0.0001 to 0.5 wt. % of a compound of the general formula

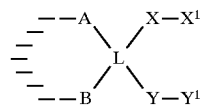

where
A and B may be the same or different and may be alkyl, alkenyl or aryl;

L is selected from the group consisting of
>CH–CH<
and >C=C< and A, B and L together can constitute part of a cyclic structure which can be aromatic, alicyclic or mixed aromatic/alicyclic, and with the proviso that the groups —X–$X^1$ and Y–$Y^1$ are located on different carbon atoms constituting L and in that when A, B and L do not constitute part of a cyclic structure one of A or B may be hydrogen and in that when L is non-cyclic ethylenic, said X–$X^1$ and Y–$Y^1$ groupings are present in a cis configuration;

X is selected from the group consisting of
—$SO_3^{(-)}$, —$S(O_2)O$—, —$S(O_2)$—, —$C(O)$—, —$CO_2^{(-)}$,
—$R^4C(O)O$—, —$N(R^3)C(O)$—,
—$R^4O$—, $R^4OC(O)$—, —$R^4$— and —$N(COR^3)$—;
when X is —$SO_3^{(-)}$ OR —$CO_2^{(-)}$
$X^1$ is selected from the group consisting of
$N^{(+)}R_3^3R^1$, $N^{(+)}HR_2^3R^1$, $N^{(+)}H_2R^3R^1$ and $N^{(+)}H_3R^1$;
when X is —$S(O_2)$— or —$C(O)$—
$X^1$ is —$NR^3R^1$;
when X is —$S(O_2)O$—, —$R^4C(O)O$—,
—$N(R^3)C(O)$—, —$R^4O$—, —$R^4OC(O)$—,
—$R^4$— and —$N(COR^3)$—
$X^1$ is —$R^1$;
Y is selected from —$SO_3^{(-)}$,
—$S(O_2)$— or —$S(O_2)O$—;
when Y is —$SO_3^{(-)}$
$Y^1$ is selected from the group consisting of
$N^{(+)}R_3^3R^2$, $N^{(+)}HR_2^3R^2$, $N^{(+)}H_2R^3R^2$ and $N^{(+)}H_3R^2$;
when Y is —$S(O_2)$—
$Y^1$ is —$NR^3R^2$;
when Y is —$S(O_2)O$—
$Y^1$ is —$R^2$;
and wherein $R^1$ and $R^2$ are straight chain or branched at the 1 or 2 position, and are independently selected from the group consisting of alkyl, alkoxy alkyl or polyalkoxyalkyl groups containing at least 10 carbon atoms in their main chain;
$R^3$ is hydrocarbyl and each $R^3$ is the same or different; and
$R^4$ is —$(CH_2)_n$ where n is from 0 to 5.

6. Distillate fuel according to claim 5 in which the groups $R^1$, $R^2$ and $R^3$ are straight chain alkyl groups containing 10 to 24 carbon atoms.

7. Distillate fuel according to claim 5 which also contains at least one other additive selected from comb polymers; polyalkylene ester, ether or ester/ether; ethylene-unsaturated ester copolymers and polar nitrogen-containing compounds.

8. Distillate fuel according to claim 5 in which one of the other additives is a copolymer of ethylene and an ethylenically unsaturated ester.

9. Distillate fuel oil boiling in the range of 120° C. to 500° C. which has a wax content of at least 0.3 wt. % at a temperature of 10° C. below the Wax Appearance Temperature and where the wax crystals at that temperature have an average particle size less than 4000 nanometres and containing an amount of a compound of the general formula

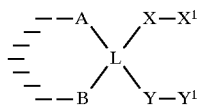

where
- A and B may be the same or different and may be alkyl, alkenyl or aryl;
- L is selected from the group consisting of
  >CH–CH<
  and >C=C<
- and A, B and L together can constitute part of a cyclic structure which can be aromatic, alicyclic or mixed aromatic/alicyclic, and with the proviso that the groups —X–$X^1$ and Y–$Y^1$ are located on different carbon atoms constituting L and in that when A, B and L do not constitute part of a cyclic structure one of A or B may be hydrogen and in that when L is non-cyclic ethylenic, said X–$X^1$ and Y–$Y^1$ groupings are present in a cis configuration;
- X is selected from the group consisting of
  —$SO_3^{(-)}$, —$S(O_2)O$—, —$S(O_2)$—, —$C(O)$—, —$CO_2^{(-)}$,
  —$R^4C(O)O$—, —$N(R^3)C(O)$—,
  —$R^4O$—, $R^4OC(O)$—, —$R^4$— and —$N(COR^3)$—;
- when X is —$SO_3^{(-)}$ OR —$CO_2^{(-)}$
  $X^1$ is selected from the group consisting of
  $N^{(+)}R_3^3R^1$, $N^{(+)}HR_2^3R^1$, $N^{(+)}H_2R^3R^1$ and $N^{(+)}H_3R^1$;
- when X is —$S(O_2)$— or —$C(O)$—
  $X^1$ is —$NR^3R^1$;
- when X is —$S(O_2)O$—, —$R^4C(O)O$—, —$N(R^3)C(O)$—, —$R^4O$—, —$R^4OC(O)$—, —$R^4$— and —$N(COR^3)$—
  $X^1$ is —$R^1$;
- Y is selected from —$SO_3^{(-)}$, —$S(O_2)$— or —$S(O_2)O$—;
- when Y is —$SO_3^{(-)}$
  $Y^1$ is selected from the group consisting of
  $N^{(+)}R_3^3R^2$, $N^{(+)}HR_2^3R^2$, $N^{(+)}H_2R^3R^2$ and $N^{(+)}H_3R^2$;
- when Y is —$S(O_2)$—
  $Y^1$ is —$NR^3R^2$;
- when Y is —$S(O_2)O$—
  $Y^1$ is —$R^2$;
  and wherein $R^1$ and $R^2$ are straight chain or branched at the 1 or 2 position, and are independently selected from the group consisting of alkyl, alkoxy alkyl or polyalkoxyalkyl groups containing at least 10 carbon atoms in their main chain;
  $R^3$ is hydrocarbyl and each $R^3$ is the same or different; and
  $R^4$ is —$(CH_2)_n$ where n is from 0 to 5.

10. Distillate fuel according to claim 9 in which the wax crystals have an average particle size less than 3000 nanometres.

11. Distillate fuel according to claim 9 in which the wax crystals have an average particle size less than 2000 nanometres.

12. Distillate fuel according to claim 9 in which the wax crystals have an average particle size less than 1500 nanometres.

13. Distillate fuel according to claim 9 in which the wax crystals have an average particle size less than 1000 nanometres.

* * * * *